US010472605B2

(12) United States Patent
Barry et al.

(10) Patent No.: US 10,472,605 B2
(45) Date of Patent: Nov. 12, 2019

(54) SERUM-FREE MEDIUM

(71) Applicant: National University of Ireland, Galway, Galway (IE)

(72) Inventors: Francis Peter Barry, Galway (IE); Emma Jane Mooney, Galway (IE); Josephine Mary Murphy, Galway (IE); Georgina Margaret Shaw, Galway (IE); Sean Patrick Gaynard, Galway (IE)

(73) Assignee: National University of Ireland, Galway, Galway (IE)

( * ) Notice: Subject to any disclaimer, the term of this patent is extended or adjusted under 35 U.S.C. 154(b) by 0 days.

(21) Appl. No.: 15/118,569

(22) PCT Filed: Feb. 16, 2015

(86) PCT No.: PCT/EP2015/053223
§ 371 (c)(1),
(2) Date: Aug. 12, 2016

(87) PCT Pub. No.: WO2015/121471
PCT Pub. Date: Aug. 20, 2015

(65) Prior Publication Data
US 2017/0044489 A1   Feb. 16, 2017

(30) Foreign Application Priority Data

Feb. 14, 2014 (EP) .................................... 14155263

(51) Int. Cl.
*C12N 5/00* (2006.01)
*C12N 5/0775* (2010.01)

(52) U.S. Cl.
CPC ......... *C12N 5/0037* (2013.01); *C12N 5/0031* (2013.01); *C12N 5/0663* (2013.01); *C12N 5/0665* (2013.01); *C12N 5/0667* (2013.01); *C12N 5/0668* (2013.01); C12N 2500/25 (2013.01); C12N 2500/36 (2013.01); C12N 2500/38 (2013.01); C12N 2501/115 (2013.01); C12N 2501/15 (2013.01); C12N 2501/39 (2013.01); C12N 2533/52 (2013.01)

(58) Field of Classification Search
CPC . C12N 5/0037; C12N 5/0031; C12N 2500/25
See application file for complete search history.

(56) References Cited

U.S. PATENT DOCUMENTS

| 4,762,792 A * | 8/1988 | Girgis ........................ C07J 9/00 435/243 |
| 5,908,782 A * | 6/1999 | Marshak .............. C12N 5/0663 424/93.7 |
| 2010/0279412 A1 | 11/2010 | Kato et al. |

FOREIGN PATENT DOCUMENTS

| JP | H11-506610 A | 6/1999 |
| JP | 2003-508046 A | 3/2003 |
| JP | 2005-512592 A | 5/2005 |
| WO | 96/39487 A1 | 12/1996 |
| WO | 1999/005301 A1 | 2/1999 |
| WO | 01/16294 A2 | 3/2001 |
| WO | 03/055989 A2 | 7/2003 |
| WO | 2005/113751 A1 | 12/2005 |
| WO | 2013/054112 A1 | 4/2013 |

OTHER PUBLICATIONS

Diffenderfer et al., The composition and metabolism of large and small LDL. Current Opinion in Lipidology, vol. 25, No. 3 (Jun. 2014) pp. 221-226.*
'Basal Medium'. Biology Online Dictionary [online]. Oct. 3, 2005 [retrieved on Sep. 21, 2018]. Retrieved from the Internet: <URL:https://www.biology-online.org/dictionary/Basal_medium>. (Year: 2005).*
R. Ian Freshney, "Defined Media and Supplements" and "Serum-Free Media". In: Culture of Animal Cell: A Manual of Basic Technique and Specialized Applications. (Hoboken, NJ, John Wiley. & Sons, Inc., 2010), pp. 99-132. H585.2.F74 2010. (Year: 2010 ).*
Lucas G Chase et al., "A novel serum-free medium for the expansion of human mesenchymal stem cells", Stem Cell Research & Therapy, Apr. 2, 2010, pp. 1-11, vol. 1, No. 1, XP021085674.
Sima Hayavi et al., Receptor dependent cellular uptake of synthetic low density lipoprotein by mammalian cells in serum-free tissue culture, Journal of Pharmacy and Pharmacology, Oct. 2006, pp. 1337-1342, vol. 58, No. 10, XP002722790.
Fenxi Zhang et al., "Lectin-like oxidized LDL receptor-1 expresses in mouse bone marrow-derived mesenchymal stem cells and stimulates their proliferation", Experimental Cell Research, Apr. 2013, pp. 1054-1059, vol. 319, No. 7, XP055187718.
Michiko Hisamatsu-Sakamoto et al., "Embryonic Stem Cells Cultured in Serum-Free Medium Acquire Bovine Apolipoprotein B-100 from Feeder Cell Layers and Serum Replacement Medium", Stem Cells 2008, pp. 72-78, vol. 26, No. 1, XP002722789.
International Search Report for PCT/EP2015/053223, dated May 26, 2015.
Written Opinion for PCT/EP2015/053223, dated May 26, 2015.

* cited by examiner

Primary Examiner — Satyendra K Singh
(74) Attorney, Agent, or Firm — Sughrue Mion, PLLC

(57) ABSTRACT

A serum-free medium for the growth of mesenchymal stem cells comprises FGF, TGF-β and lipoprotein.

15 Claims, 19 Drawing Sheets

Fig. 3
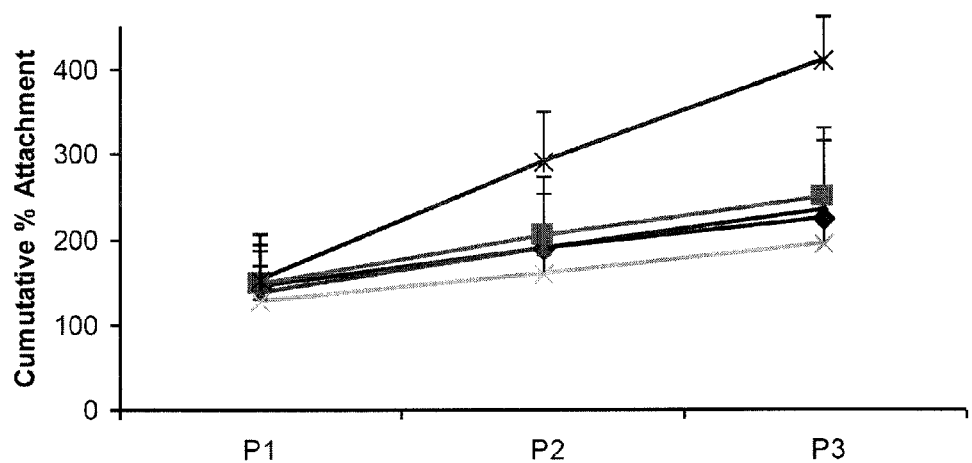
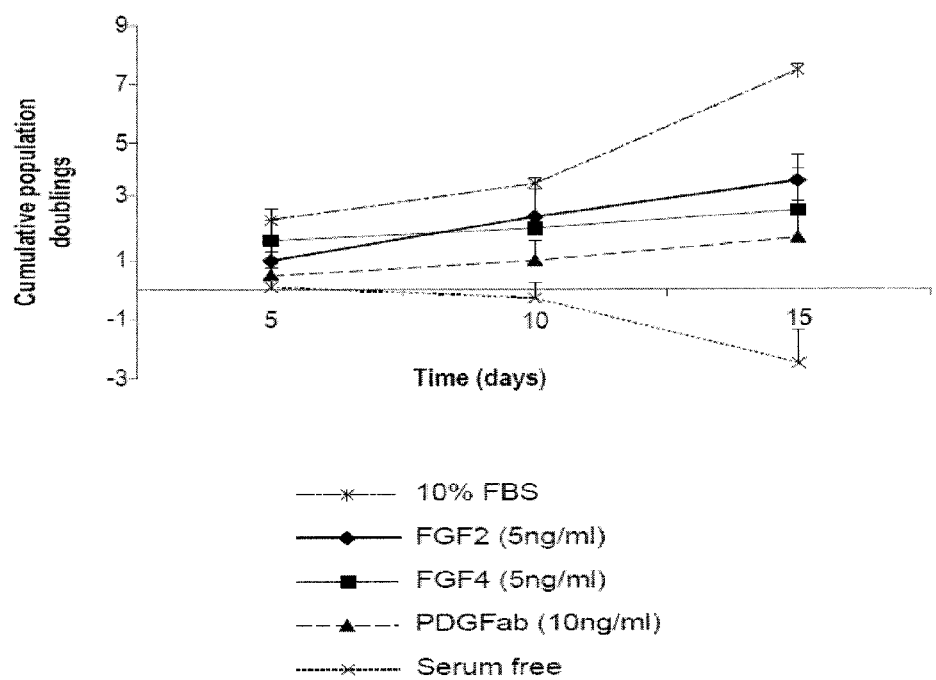
*Fig.4*

Fig. 6
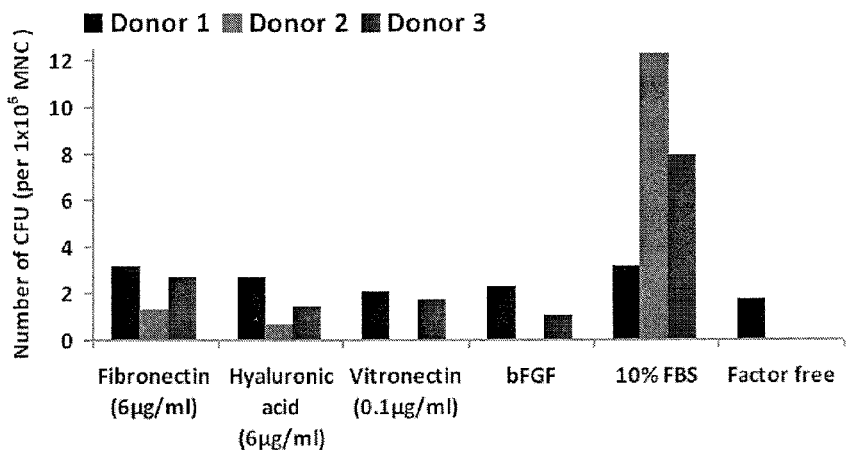
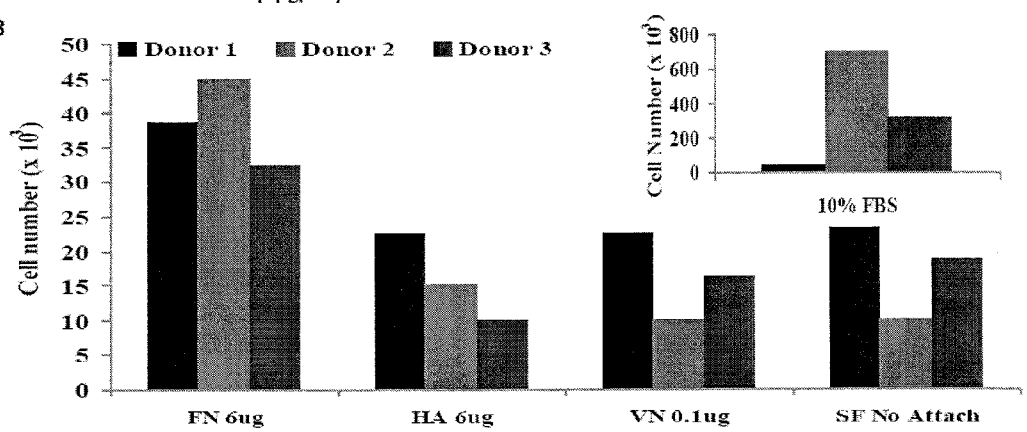
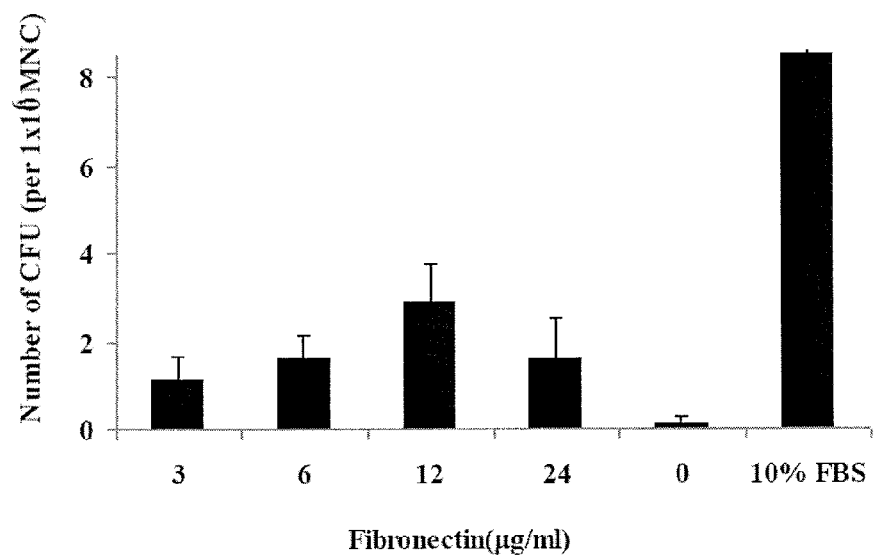

Fig. 7
A
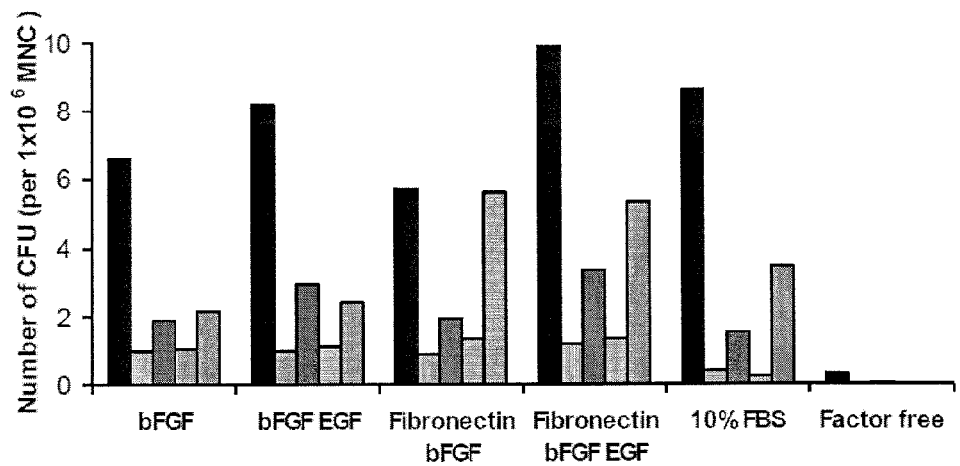
B
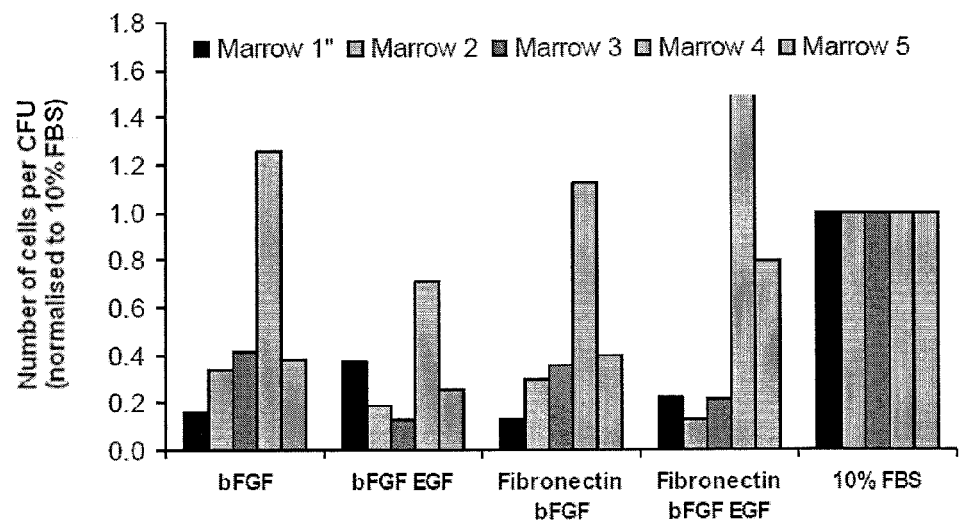

c

Fig. 14
A
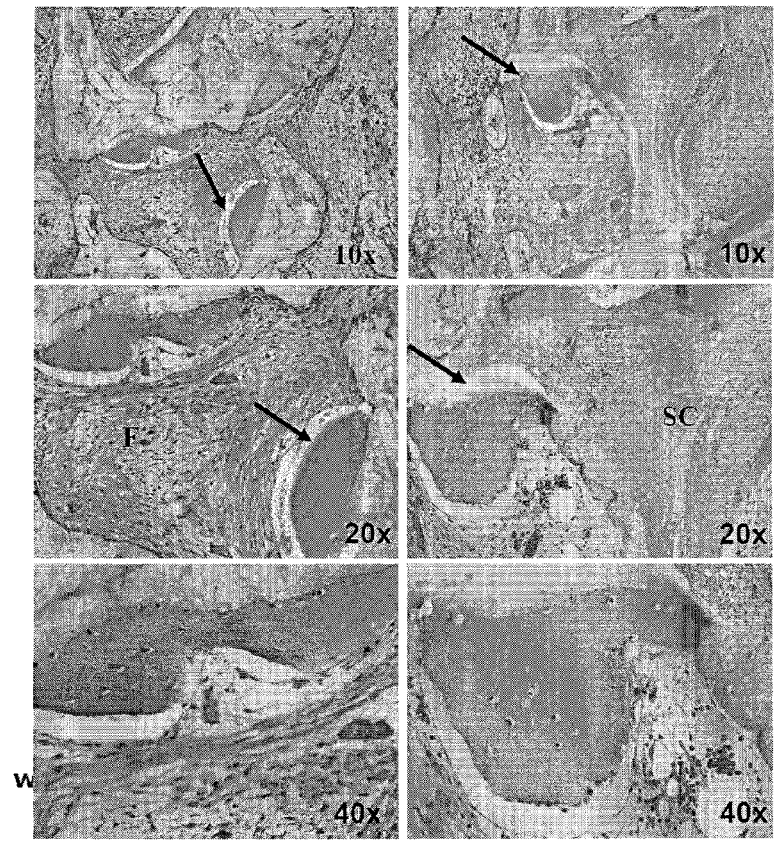
Sample #94 TGF-B
2 different implants
→ vessel
→ bone
SC skelite scaffold
F fibrous tissue
B
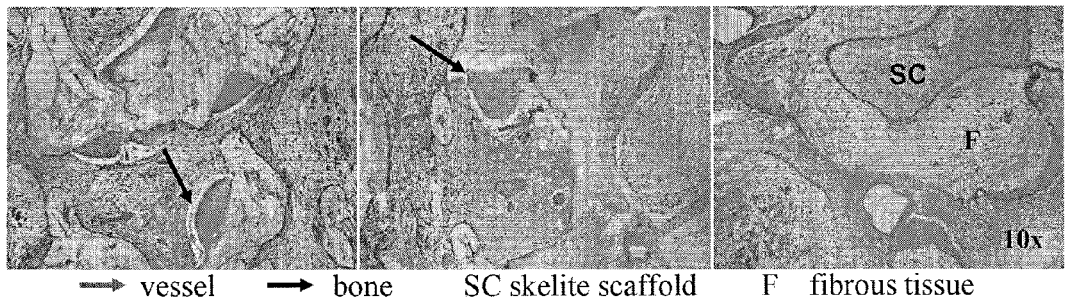
→ vessel   → bone   SC skelite scaffold   F fibrous tissue

Sample #92 TGF-B
2 different implants

⟶ vessel
⟶ bone

SC skelite scaffold
F fibrous tissue

Fig. 16
A
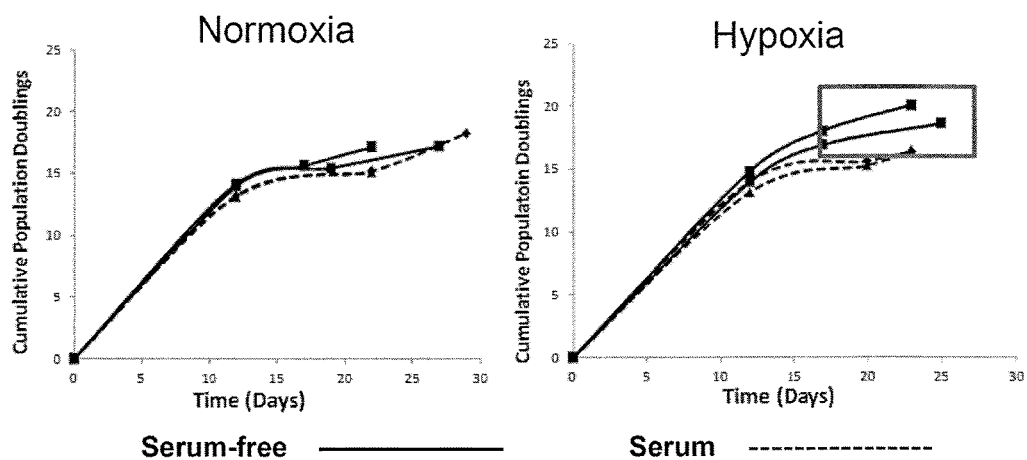
B
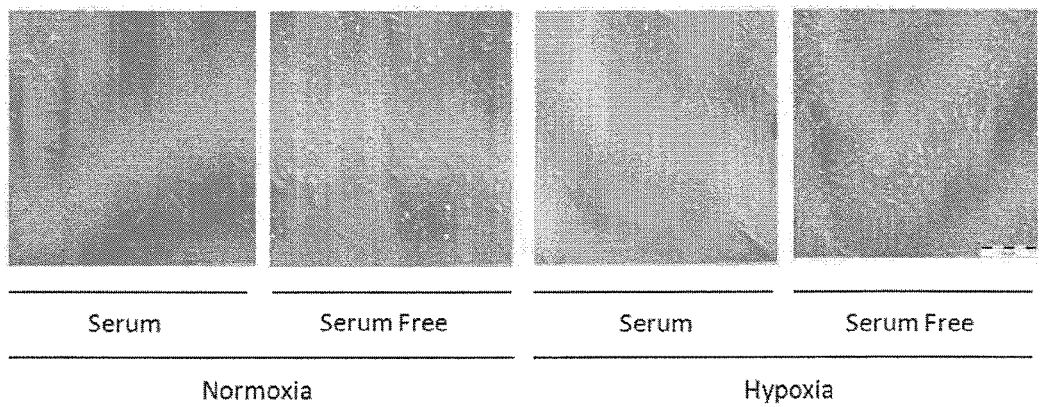
C
Predicted Yields (30mL marrow)

SERUM-FREE MEDIUM

CROSS REFERENCE TO RELATED APPLICATIONS

This application is a National Stage entry of International Application No. PCT/EP2015/053223, filed Feb. 16, 2015, which claims priority to European Patent Application No. 14155263.8, filed Feb. 14, 2014, the contents of all of which are incorporated herein by reference in their entirety.

FIELD OF THE INVENTION

The present invention relates to a medium for the growth of stem cells without the use of serum as a component of the medium, methods for utilising this medium and cells produced using this medium.

BACKGROUND

Mesenchymal stem cells (MSC) are multipotent cells that can differentiate into a variety of cell types, including: osteoblasts (bone cells), chondrocytes (cartilage cells) and adipocytes (fat cells). This capability has been demonstrated for specific cells and tissues in living animals and for their counterparts grown in tissue culture.

MSC are a valuable resource for cell-based drug discovery and a potential therapeutic for a number of human diseases. The potential of MSC to treat disorders including graft-versus-host disease, multiple sclerosis, Crohn's disease, type 1 diabetes, bone fractures and osteoarthritis is currently being examined in clinical settings.

It is estimated that MSC comprise a mere 0.001 to 0.01% of total bone marrow mononuclear cells; therefore, this population requires extensive in vitro cell culture expansion to obtain sufficient numbers for basic biological or clinical applications. Current clinical applications use an approximate dose of 100 million cells.

Current developments in regenerative medicine and cellular therapy suggest that there will be an extraordinary increase in cell processing technology in the coming years. This will relate to adult and embryonic stem cells as well as somatic cells used for therapeutic purposes. In addition, the increased use of stem cells and induced pluripotent stem cells in drug screening applications will see the demand for cell processing technology increase greatly.

Isolation and culture of these MSC relies for the most part on the use of animal products, in particular foetal bovine serum (FBS).

Stem cells require specific growth conditions. Currently, bone marrow-derived MSC are isolated, cultured and differentiated in serum-containing medium.

Virtually all mammalian cells grown in laboratory culture require the presence of FBS in the growth medium, which provides hormones and growth factors necessary for cell attachment and proliferation. This includes human cells currently under investigation for therapeutic use, such as adult and embryonic stem cells and other somatic cells. FBS is harvested from the blood of foetal calves obtained in the meat processing industry and is generally added to growth media at a concentration of 10% by volume. Consequently, the supply of stem cells is dependent on the availability of suitable media to grow them in.

This technique has been successfully applied for several decades and FBS is the most commonly used growth medium supplement because of the complex mixture of proteins and high levels of growth-stimulatory factors present in foetal blood. However, there are problems associated with the use of FBS, some of which are listed below:

1. Risk of disease transmission to recipients of cellular therapy
2. Risk of disease transmission to processing technicians and medical personnel
3. Uncertain and seasonal availability of product
4. Need for cryostorage at −20° C.
5. Significant batch-to-batch variability.
6. Anticipated major supply-chain problems because of increased demand.

A major concern associated with the use of FBS in cells produced for human therapy is the risk of transmission of infectious material to the recipient. In addition there is considerable risk associated with the handling of these materials by processing technicians and medical staff. This risk has become starkly serious in recent years because of the emergence of transmissible bovine spongiform encephalopathy (BSE), commonly known as mad-cow disease, and the associated risk to humans of acquiring variant Creutzfeldt-Jakob disease (vCJD). To date, BSE has been detected in cattle in Europe, North America and in many other parts of the world. Almost all FBS now approved for use in the growth of cells for human therapy comes from Australia and New Zealand, which are still BSE free.

The emergence of BSE in cattle herds throughout the world has also lead to a major supply problem, and this is predicted to have a serious impact on the availability of cellular therapies in the future. Currently this limited supply of serum is generally sufficient for laboratory and research use. However, some of these laboratory and research uses are directed to producing a commercial product that will be produced on a medium or large scale. Currently there are no applications for stem cell technologies that are approved for general use. Thus, it can be envisioned that when a stem cell technology is released for general use the supply of serum will simply not be adequate to meet this demand.

Indeed, it is anticipated that, when cellular therapy products are approved for just two major indications, the entire global supply of approved, BSE-free FBS will be consumed within the first year of manufacturing. Thus, as cellular therapies gain regulatory approval and are used there will be an extraordinary and unprecedented demand for FBS-free growth medium. Clearly, the supply of stem-cell growth medium will be a limiting factor in the application of stem-cell technologies.

In addition, FBS is a heterogeneous mixture, which leads to a lack of reproducibility and performance between serum batches. Serum contains many unidentified or non-quantified components and therefore is not "defined" and cannot be recreated synthetically. Consequently, the composition of serum varies from batch-to-batch, making standardization difficult for experimentation or other uses of cell culture. Also, MSCs are an adherent cell population and currently this capacity to adhere to tissue culture plastic relies on FBS for the most part.

Indeed, because many of the components of FBS affect cell attachment, proliferation and differentiation, controlling these parameters, or studying the specific requirements of cells with respect to these parameters, is precluded by the use of serum. Furthermore, some components of serum are inhibitory to the proliferation of specific cell types and to some degree may counteract its proliferative effect, resulting in sub-optimal growth.

The variability in growth characteristics caused by the heterogeneous nature of FBS leads to a lack of reproducibility between serum batches and presents problems for growth and manufacturing of cell-based products and therapies. This is particularly the case for products made under Good Manufacturing Protocols (GMP) which are presupposed to operate using consistent, and therefore reliable, starting materials.

Furthermore, from a therapeutic and regulatory standpoint, the presence of FBS is not ideal as this may lead to the transfer of animal pathogens. While serum is approved for medical use, it may contain viruses which may affect the outcome of experiments or provide a potential health hazard if the cultured cells are intended for implantation in humans. Furthermore, from a regulatory point of view, the use of animal-derived products in a clinical setting is undesirable not only because of the risk of transmission of infectious agents but also the potential to evoke an immune response.

Thus there is a need for a growth medium for the propagation and/or production of stem cells that does not need to be supplemented with serum. Any such new growth medium should preferably be relatively simple and easy to produce in large quantities.

Consequently, efforts have been made to eliminate FBS from culture media and develop a defined serum free medium capable of ex vivo expansion of MSC.

WO 2011/111787 discloses a cell preparation that contains mesenchymal stem cells which maintain immunosuppressive ability, produced by serum-free or low-serum culture. A method for producing a cell preparation containing mesenchymal stem cells is described that comprises: a proliferation step wherein mesenchymal stem cells are proliferated in a culture medium that contains FGF, PDGF, TGF-β, HGF, EGF, at least one phospholipid and at least one fatty acid; and a screening step wherein the mesenchymal stem cells after the proliferation step are screened for mesenchymal stem cells in which the immunosuppressive ability is maintained or improved.

WO 98/104681 discloses a serum-free defined cell culture medium comprising a supplement mixture, a component mixture, a vitamin mixture, an inorganic salt mixture and an amino acid mixture. This defined medium is disclosed as being useful for culturing fibroblasts, especially chondrocytes. Also disclosed is a method of enhancing the differentiation of chondrocytes and enhancing the synthesis of a cartilage specific matrix using tumor growth factor beta (TGF-β) and a method of enhancing the differentiation of chondrocytes using the combination of TGF-β and insulin-like growth factor (IGF).

Other media for MSC have been proposed. WO 2005/113751 describes expansion of MSC in serum-free media; the media are highly complex and some can contain, inter alia, bFGF and TGF-beta. US 2010/0279412 also describes serum-free media, which may contain a FGF, a TGF, an EGF, phosphatidic acid, phosphatidylcholine and vitamin C. Chase et al, Stem Cell Research & Therapy 2010, 1:8 describe a serum-free medium for human MSC, containing bFGF, TGF-beta1 and PDGF.

It is an object of the present invention to provide a medium and methods for the growth of stem cells that represents at least an alternative to the above, and preferably solves or at least ameliorates one or more problems identified in the prior art. An object of specific embodiments is to provide a medium for the growth of MSC that does not require supplementing with serum and thus is easily available and relatively inexpensive.

SUMMARY OF THE INVENTION

Accordingly, the invention provides a serum-free medium for culturing stem cells comprising:

(a) fibroblast growth factor (FGF);
(b) transforming growth factor beta (TGF-β); and
(c) lipoprotein.

An advantage of the invention is that it enables production of a medium that is a fully FBS-free, i.e. a serum-free, growth medium that is suitable for propagation of stem cells and tissue culture, especially mesenchymal cells, especially human cells and tissue.

In addition, the medium of the invention is suitable for directly propagating cells isolated from bone marrow, i.e. such isolated cells can be placed straight into the medium of the invention for growth without first requiring incubation or propagation in a serum-containing medium.

An additional advantage of the medium of the invention is that cells cultured in it under hypoxic conditions may display superior growth kinetics.

A further advantage of using the medium of the invention to grow cells is that such use can increase the yield of cells, as compared with prior-art, serum-based media. The medium of the present invention potentially allows a manufacturer to obtain a much higher yield of cells (at least tenfold more) than under previously used conditions. Thus, production costs per dose are reduced by approximately 90%. Consequently, in addition to the enhanced growth characteristics of the cells in the medium of the present invention, this medium has the potential to improve the competitiveness of clinical manufacturing organisations engaged in the manufacture of MSC-based products for clinical trial and use. Currently, the cost of producing the large numbers of MSC required for clinical use under GMP-compliant conditions is one of the major concerns of companies developing regenerative medicine therapies.

Furthermore, this defined medium can be entirely manufactured to GMP-compliant standards in a scalable manner and is suitable for use in growing human cells for use. This serum free medium of the invention thus allows for greater reproducibility in the course of in vitro cell culture research.

Consequently, some further advantages of the medium of the invention are:

manufacturers are no longer constrained by the uncertainties of FBS supply removal of the risk of disease transmission, since all of the raw materials can be sourced from GMP suppliers overcoming the problems of batch variability seen in serum-based growth media; additionally, since the serum-free medium has a defined composition, the requirement for manufacturers or investigators to "batch test" serum lots is negated.

The use of serum-free media thus provides significant reassurance for regulatory bodies as cellular therapies move from experimental to clinical use. It also dramatically reduces the cost of large-scale production of MSC, particularly for GMP cultured cells for therapeutic use where the cost of production of a single clinical dose is prohibitively expensive due to the poor yield of cells per production run.

The medium may also comprise epidermal growth factor (EGF), suitably at a concentration of from 1 to 100 ng/ml, preferably from 2 to 50 ng/ml or from 2 to 25 ng/ml; in a specific example, EGF is present in the medium at about 10 ng/ml. The medium may also comprise fibronectin, suitably at a concentration of from 1 to 100 µg/ml, preferably 1 to 24 µg/ml.

An advantage of including EGF and fibronectin in the medium of the invention flows from noting that, in use, such a medium yielded the most cells per colony forming unit (CFU) from samples taken directly from bone marrow.

Lipoproteins are complex particles which transport cholesterol, phospholipids, and triglycerides around the body. They include, from largest to smallest (least dense to densest), chylomicrons (ULDL), very low-density lipoprotein (VLDL), intermediate-density lipoprotein (IDL), low-density lipoprotein (LDL), and high-density lipoprotein (HDL). These are terms recognised and well known and understood in the art and used extensively in the literature without further definitions.

Low-density lipoprotein (LDL) hence refers to a class and range of such lipoprotein particles, varying in size generally from about 15 or from about 18 to about 30 nm, or to about 25 nm, in diameter (laser based methods can be used for this measurement). LDL particles typically contain a single apolipoprotein B-100 molecule (Apo B-100), along with very approximately 80 to 100 additional ancillary proteins. Each LDL typically has a highly hydrophobic core consisting of polyunsaturated fatty acid known as linoleate and hundreds to thousands (about 1500 is commonly cited as an average) esterified and non-esterified cholesterol molecules. This core can also carry varying numbers of triglycerides and other fats and be surrounded by a shell of phospholipids and unesterified cholesterol, as well as the single copy of Apo B-100. Some specific LDL particles are approximately 22 nm in diameter and have a mass of about 3 million daltons, though in general the term LDL is known in the art and embraces particles falling within the above defined parameters. In the typical human body, since LDL particles contain a variable and changing number of fatty acid molecules, there is a distribution of LDL particle mass and size.

Very low-density lipoprotein (VLDL) generally contains Apo B-100, ApoC1, ApoE, cholesterol, cholestryl esters, and triglycerides. As it circulates in blood, VLDL may pick up other components, and this and other changes may in time convert the VLDL to other lipoprotein forms. Again, the term VLDL is well known in the art, and typically VLDL particles have a diameter of from about 30 to about 80 nm. In the body VLDL tends to transports endogenous products, in contrast to, say, chylomicrons that tend to transport exogenous products.

Intermediate-density lipoprotein (IDL) particles tend to contain multiple copies of the receptor ligand ApoE in addition to a single copy of ApoB-100, being generally from about 25 to 35 nm in diameter. Lastly, high density lipoprotein (HDL) particles are the highest density and smallest size, generally being from about 7 or 8 to about 11 or 12 nm in diameter.

The medium may comprise one or more or all of the following:
 high-density lipoprotein (HDL);
 low-density lipoprotein (LDL);
 intermediate-density lipoprotein (IDL);
 very-low-density lipoprotein (VLDL); and
 chylomicrons.

In preferred embodiments of the invention, the medium comprises LDL or VLDL. In use as described in examples below in further detail, medium containing LDL and medium containing VLDL gave better cell growth and promoted growth of cells with desired morphology.

Preferably the medium comprises LDL, which may comprise one or more of:
 large buoyant LDL (lb LDL) particles,
 small dense LDL (sd LDL) particles, and/or
 lipoprotein(a) (Lp(a)).

It is believed that the lipoprotein is essential because it supplies cholesterol and phospholipids which cannot easily be supplied by any other means. Suitable levels of lipoprotein are 1 µg/ml or more, 2 µg/ml or more, 5 µg/ml or more and separately up to 100 µg/ml, up to 80 µg/ml or up to 60 µg/ml. In specific examples the concentration was about 4 µg/ml and about 40 µg/ml.

In examples set out in more detail below, increased numbers of colony forming units-fibroblasts (CFU-fs) were obtained with media containing VLDL or LDL. The morphology of the cells comprising the CFU-fs themselves, when VLDL or LDL was present, was also improved. With media that contained HDL the CFU-fs comprised dense clusters of cells in which some outgrowth occurred. This is atypical of CFU-fs seen when isolated in medium containing fetal bovine serum. Conversely, CFU-fs obtained using media containing either VLDL or LDL had a dispersed morphology which more closely resembled the typical CFU-f morphology associated with MSCs.

In addition to this, in further examples of the invention described in more detail below, we assessed whether 1) the addition of fibronectin to the serum-free medium formulation precluded the requirement of pre-coating with the attachment factor and 2) or whether fibronectin was needed at all for isolation and proliferation of MSCs from bone marrow with the serum-free medium formulation. No observable difference was observed between MSC cultured in media of the invention in the presence or absence of fibronectin, whether in CFU-f number or subsequent proliferation rates. This indicates that the serum-free medium formulation does not require an attachment factor for isolation or proliferation of MSC, e.g. from bone marrow.

The FGF component of the medium may comprise one or more of: FGF1, FGF2 (bFGF), FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23; preferably one or more of FGF1, FGF2 (bFGF), FGF3, FGF4, FGF5, FGF6, FGF7, FGF8, FGF9 and FGF10; most preferably the medium comprises FGF2 (bFGF). Preferably the FGF is present at a concentration of 0.5 ng/ml or more, 1 ng/ml or more, up to 50 ng/ml, up to 30 ng/ml, up to 20 ng/ml, up to 10 ng/ml or any combination of these ranges. A concentration of from 1 to 20 ng/ml is particularly suitable. In specific examples, about 5 ng/ml was used successfully. The TGFβ component of the medium may comprise one or more of: TGFβ-1, TGFβ-2 and TGFβ-3, preferably TGFβ-1. Preferably the TGFβ is present at a concentration 0.5 ng/ml or more, 1 ng/ml or more, up to 50 ng/ml, up to 30 ng/ml, up to 20 ng/ml, up to 10 ng/ml or any combination of these ranges. A concentration of from 1 to 20 ng/ml is particularly suitable. In specific examples, about 5 ng/ml was used successfully.

The serum-free medium may also comprise or be based upon a basal medium (also serum-free), intended to provide essential minerals, salts and vitamins. Basal media are well known in the art, and one such medium is Minimum Essential Medium Eagle-Alpha Modification (MEM-α). Other such basal media are available from STEMCELL Technologies SARL, France and from StemCells, Inc, USA, and still others will be known to those skilled in the art and are suitable for use in the serum-free medium of the invention.

The medium may also suitably comprise other components such as dexamethasone, human serum albumin and/or insulin-transferrin-selenium (ITS). A specific medium comprises 1% ITS, 10 nM dexamethasone, 50 mg/ml human serum albumin in MEM-α. The medium may be based upon or comprise other basal media. Additionally, the medium may contain no other or further growth factors.

In addition to uses described elsewhere herein, the medium can be used to isolate cells from donors, especially from human donors. The medium can also be used to convert cells isolated and/or grown in serum-containing conditions to serum-free. Hence, for example, cells (e.g. human cells) may be isolated using any medium or conditions then converted to grow under serum-free conditions by steps comprising culturing the cells in the presence of a medium of the invention.

The invention also provides a method of culturing a stem cell in the medium of the invention, the method comprising incubating the stem cell in the medium. The cell cultured using the method may be one or more mesenchymal stem cells (MSC). Advantageously, MSC grown in medium of the invention retain osteogenic, chondrogenic, adipogenic and/or angiogenic potential. Cells, in particular MSC, in the presence of the medium of the invention and/or cultured therein may have advantageously immunosuppressive properties.

Accordingly, the invention also provides a stem cell cultured in the medium of the invention, preferably the stem cell is a mesenchymal stem cell, even more preferably the cell is an osteogenic, chondrogenic, adipogenic and/or angiogenic cell.

Similarly, the invention also provides a population of osteogenic, chondrogenic, adipogenic and/or angiogenic cells defined above.

The invention also provides a stem cell in the medium of the invention, e.g. for use as a medicament. The invention further provides a stem cell in the medium of the invention for use in screening applications, e.g. drug screening.

An advantage of supplying a stem cell in the medium of the invention for use as a medicament is that a single growth medium is required to go from initial isolation of a stem cell to implantation of the stem cell or cells grown from the isolated stem cell. In other words, no separate medium for the isolation or implantation steps is required. This significantly simplifies the process of producing and using a stem cell or stem cell line. In addition, this reduces the risk of infection associated with multiple, generally serum-based culture media by replacing these media with a single, all-purpose serum-free culture medium.

Preferably the stem cell in the medium of the invention is for use in the formation of one or more of the following tissues:
 (a) bone tissue;
 (b) blood vessel tissue;
 (c) cartilage tissue; and/or
 (d) adipose tissue.

Advantageously, in vivo differentiation of serum-free cultured MSC to bone tissue was superior to the control experiment in which MSC were cultured in serum-containing medium.

The invention is now illustrated with reference to the following specific examples and the accompanying drawings in which:

FIG. 1 shows the degree of relative attachment of MSC isolated in 10% FBS and re-attached under serum-free conditions in the presence of bFGF 18 hours after plating. Tissue culture flasks were pre-coated with fibronectin (FN; black), hylauronic acid (HA; blue), vitronectin (VN; red) or laminin (LN; green) and cells were allowed to adhere in serum-free conditions. Controls include serum-free plating without the presence of an extra-cellular matrix (ECM) attachment factor and 10% FBS (grey). Results are representative of 3 biological replicates with n=2;

FIG. 2 shows the growth of MSC isolated in 10% FBS and re-attached under serum-free conditions in the presence of bFGF relative to serum-free conditions. Tissue culture flasks were pre-coated with FN (black), HA (blue), VN (red) or LN (green) and cells were allowed to adhere in serum-free conditions. Cell numbers were obtained after 5 days. Controls include serum-free plating without the presence of an ECM attachment factor and 10% FBS (grey). Results are representative of 3 biological replicates with n=2;

FIG. 3 shows the degree of attachment of MSC isolated in 10% FBS and re-attached under serum free conditions containing FGF2 over the course of 3 passages (P). MSC were attached on tissue culture flasks in the presence of EGF (red) or on tissue culture plastic precoated with FN (purple) or in the presence of EGF on fibronectin coated plastic (green) and passaged every 3 days. Controls include serum free plating without the presence of an ECM attachment factor (blue) and 10% FBS (black). Results are representative of 3 biological replicates with n=2;

FIG. 4 shows the growth of MSC isolated in 10% FBS and re-attached under serum-free conditions on tissue culture flasks pre-coated with FN for 2 days. Cells were then cultured in the presence of growth factors and passaged every 5 days. Controls include serum free plating without growth factors and 10% FBS. Results are representative of 3 biological replicates with n=2;

FIG. 5 shows the growth of MSC isolated in 10% FBS and re-attached under serum-free conditions on tissue culture flasks pre-coated with FN for 2 days. Cells were then cultured in serum-free media containing FGF2 (5 ng/ml) in the presence of PGE2, cholesterol or lipoprotein for 5 days. Controls include serum free plating without growth factors 10% FBS (A). Cells were then cultured in the presence of lipoprotein and passaged every 5 days for 3 passages, controls include serum free plating without lipoprotein (B). Results are representative of 3 biological replicates with n=2;

FIG. 6 shows the results of examples in which MSC were isolated from bone marrow on tissue culture plastic pre-coated with fibronectin (FN), vitronectin (VN) or hyaluronic acid (HA) in serum-free (SF) medium containing FGF2 to determine a suitable extracellular matrix for serum free MSC isolation. The number of colony forming units (CFU; FIG. 6A) and cell number (FIG. 6B) was determined at the end of primary culture. An additional marrow was seeded on tissue culture plastic pre-coated with varying concentrations of fibronectin to determine optimal concentration of fibronectin required. The number of CFU (FIG. 6C) and cell yield (FIG. 6D) was determined at the end of primary culture. Controls include MSC isolation in the presence of 10% FBS or on non-coated tissue culture plastic;

FIG. 7 shows the results of examples in which MSC were isolated from bone marrow on tissue culture plastic pre-coated with fibronectin and/or in the presence of EGF. The number of colony forming units (FIG. 7A) and cell number (FIG. 7B) was determined at the end of primary culture. Controls include MSC isolation in the presence of 10% FBS or on non-coated tissue culture plastic;

Figure 10:
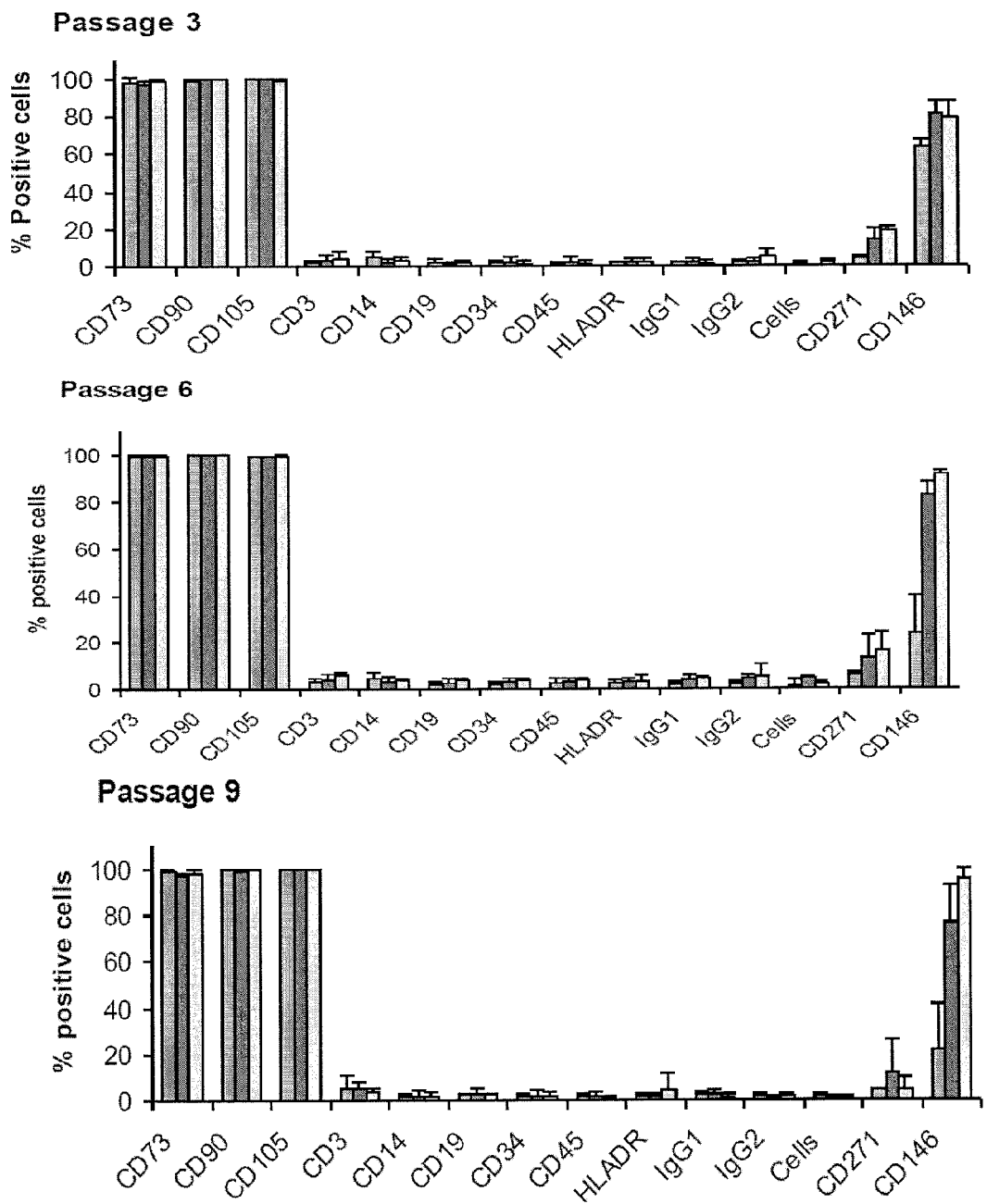
Figure 11:
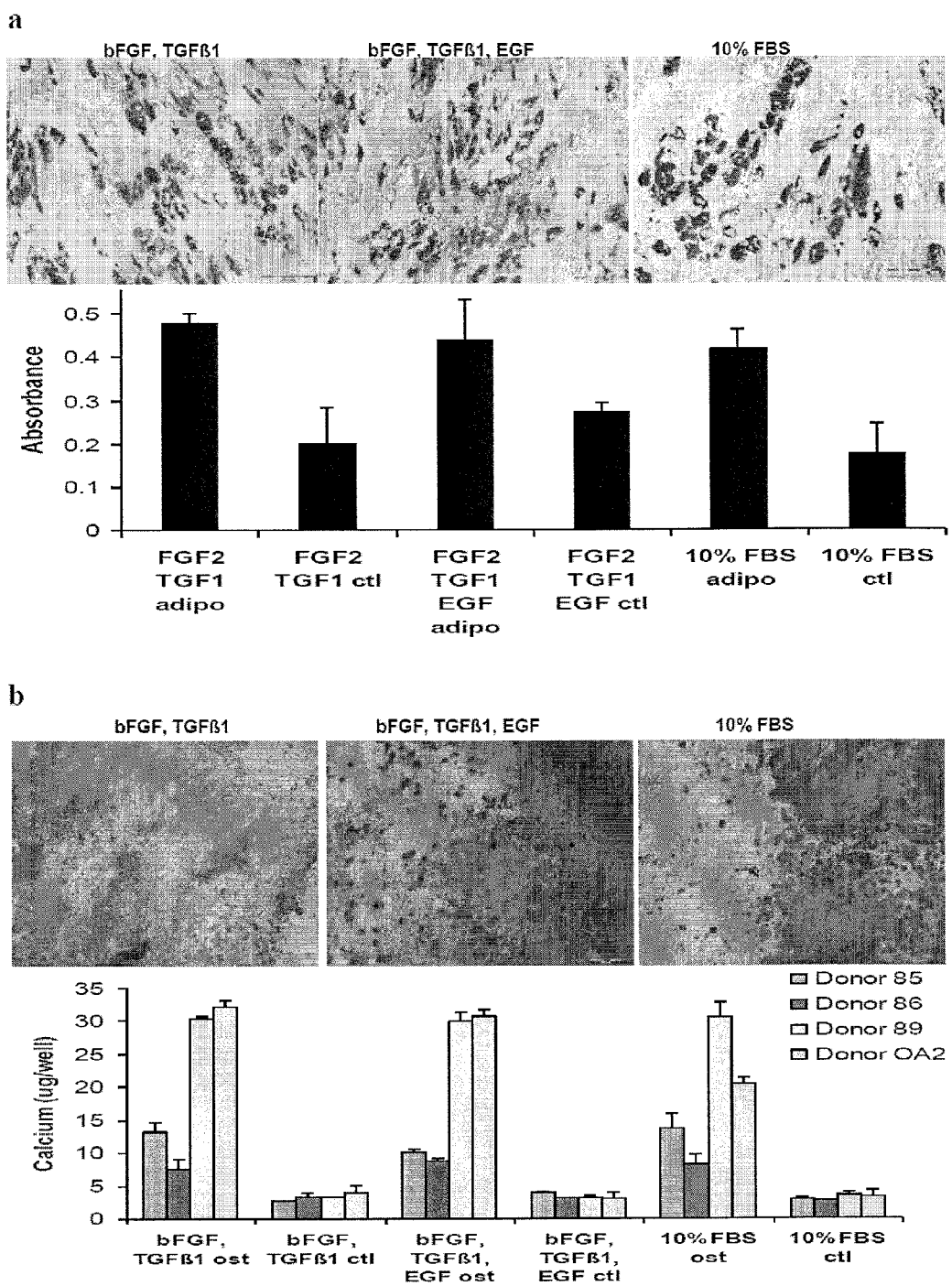
Figure 11:
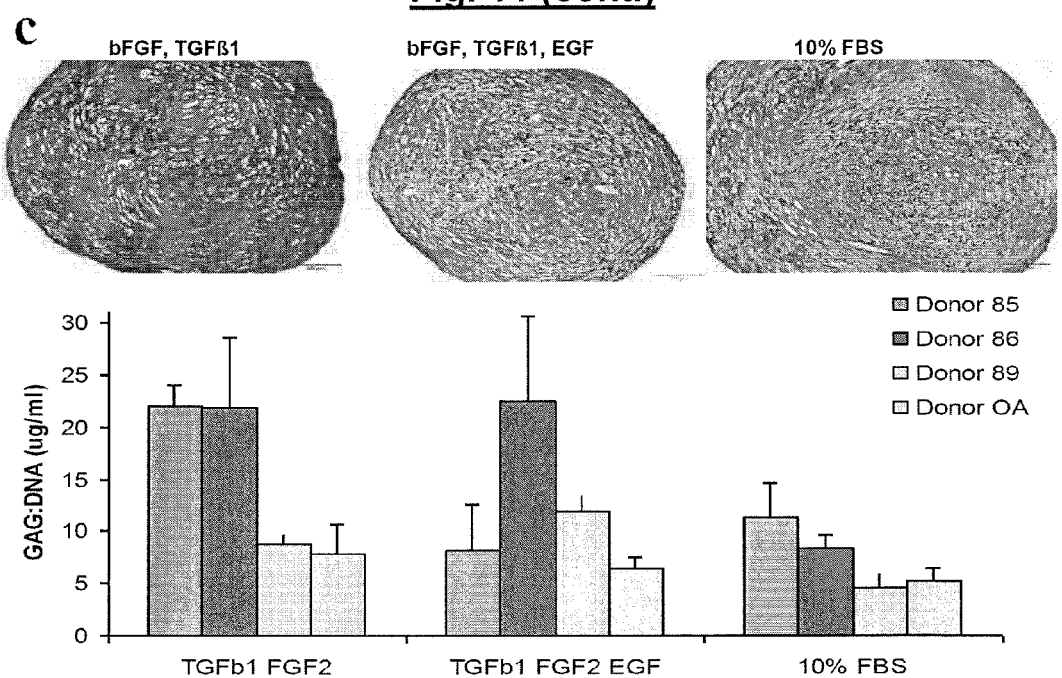
Figure 12:
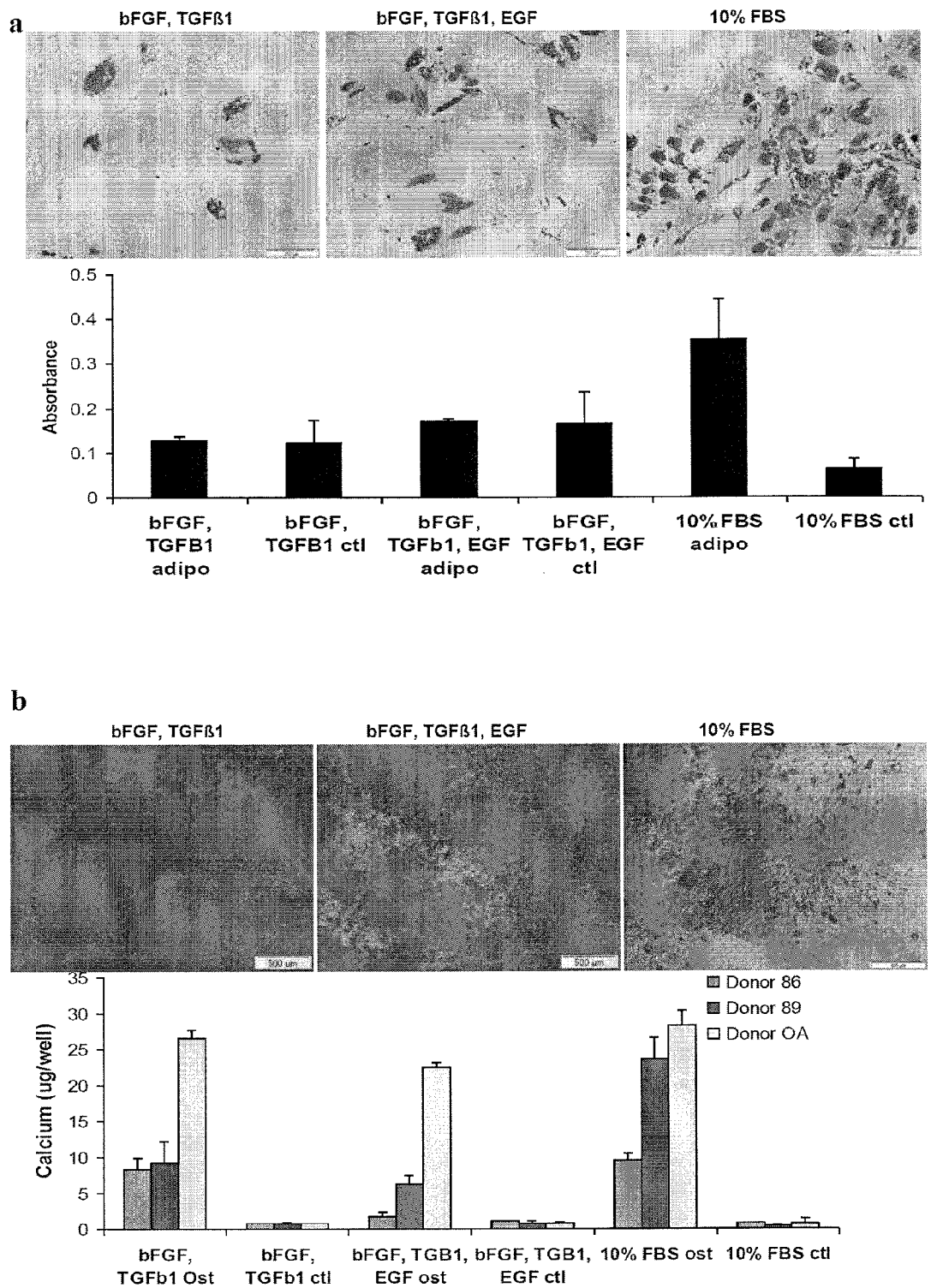
Figure 12:
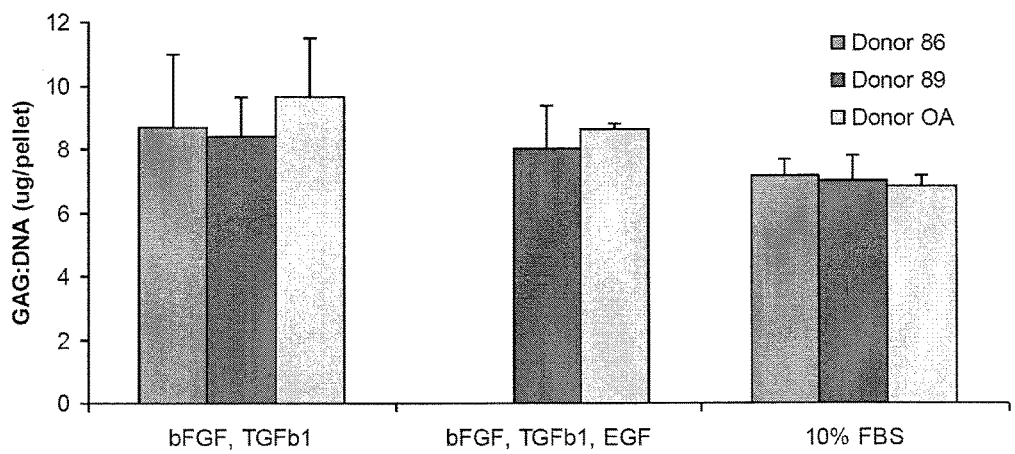
Figure 13:
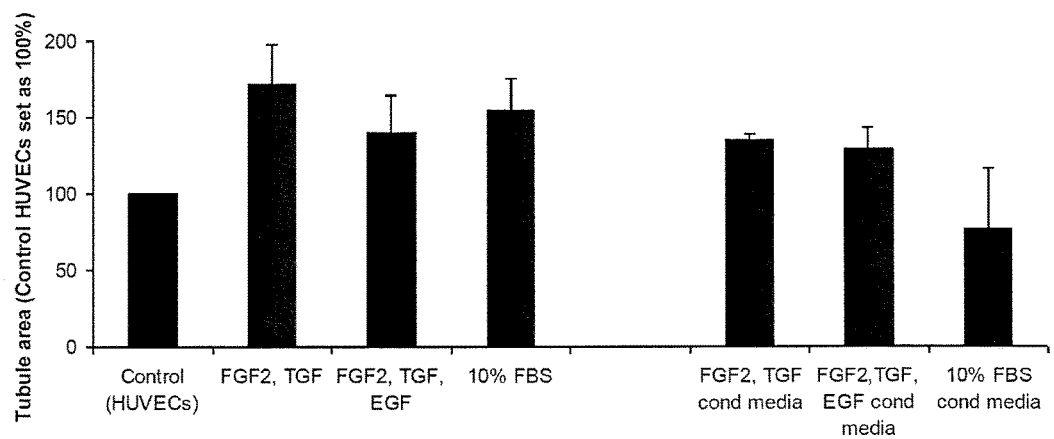
Figure 15:
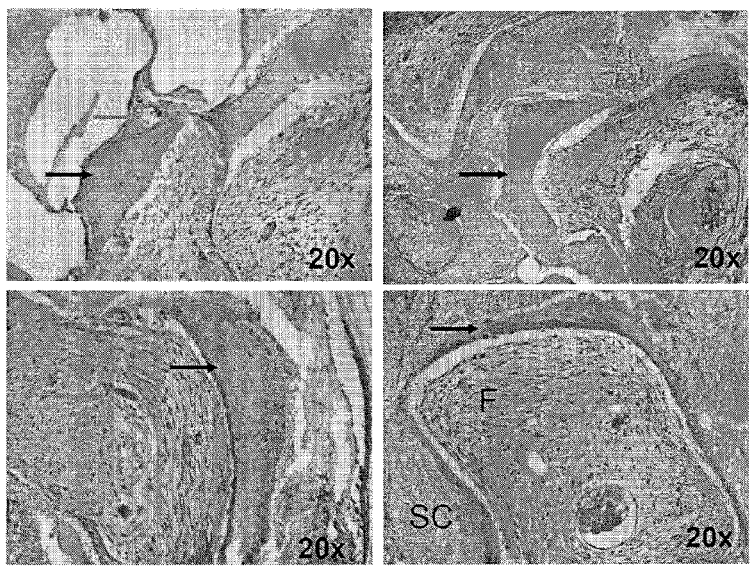
Figure 17:
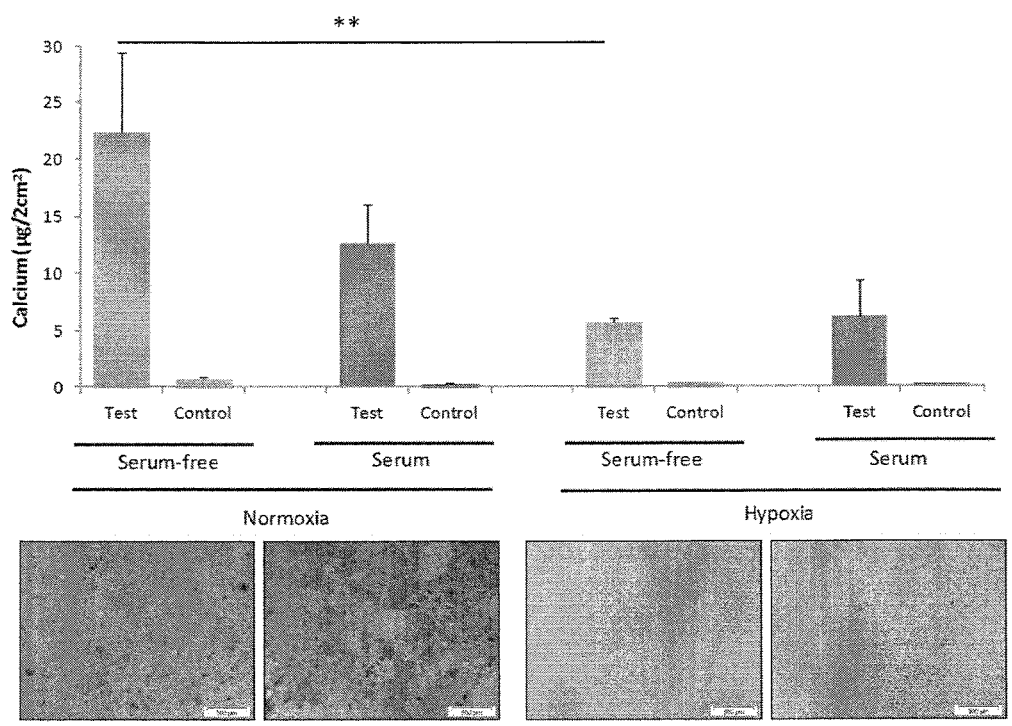
Figure 18:
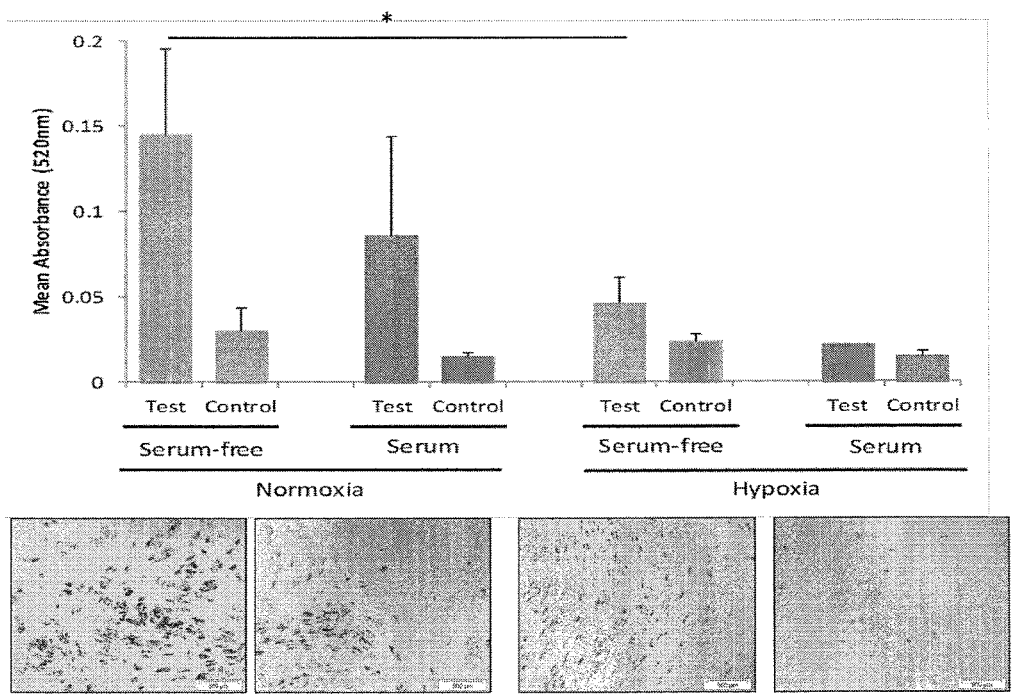
Figure 19:
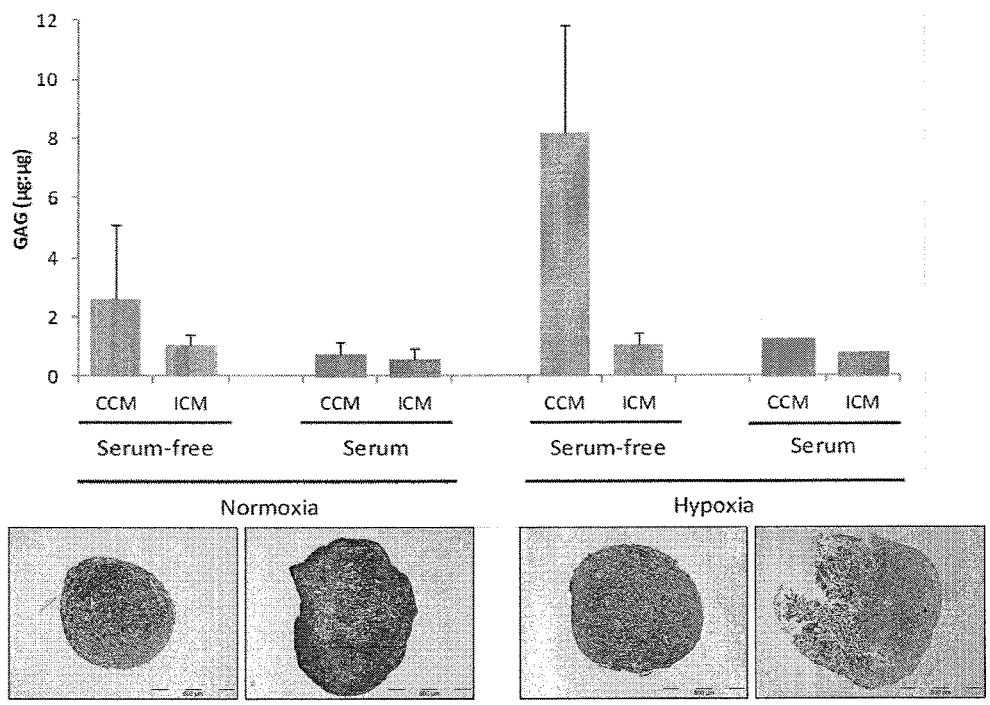
Figure 20:
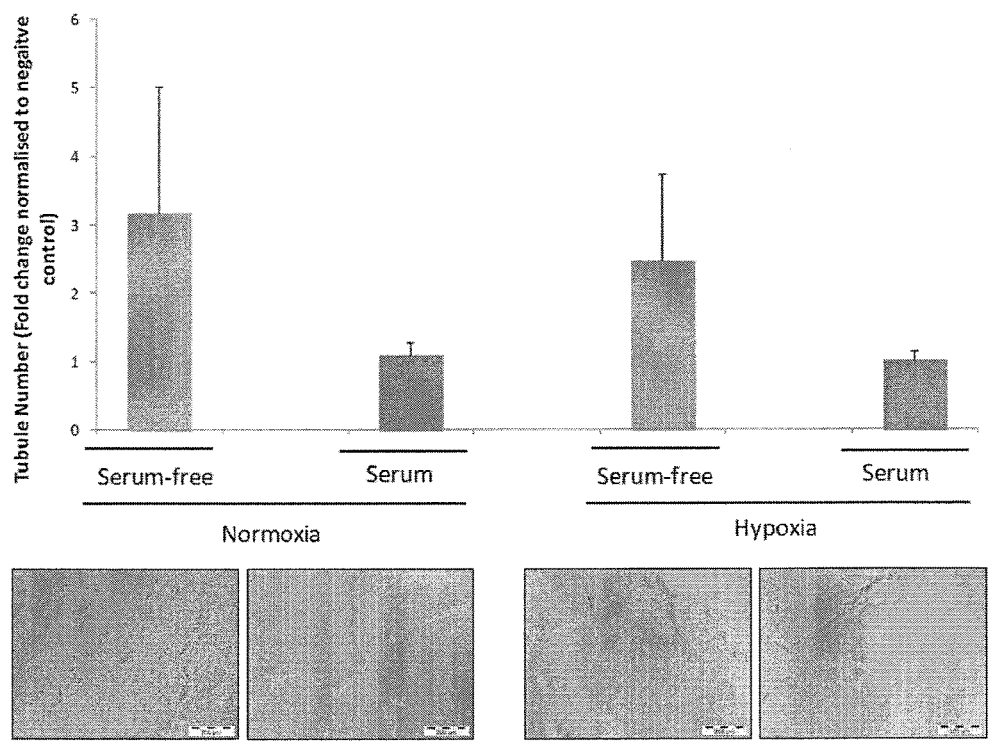
Figure 21:
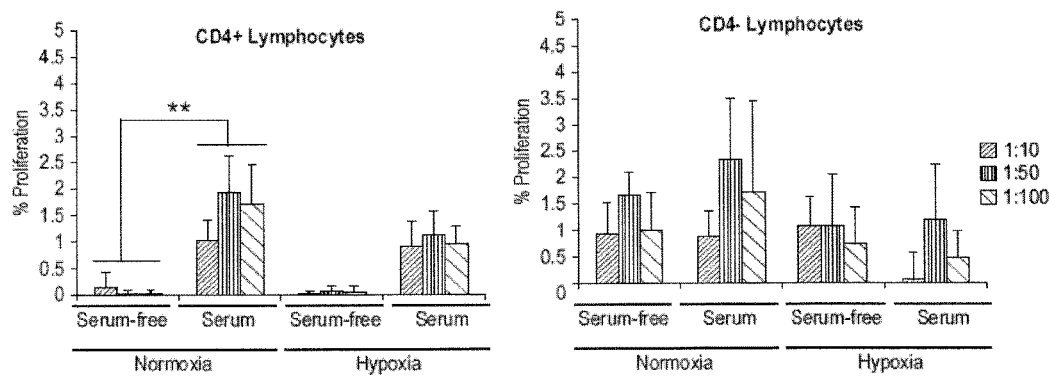
Figure 22:
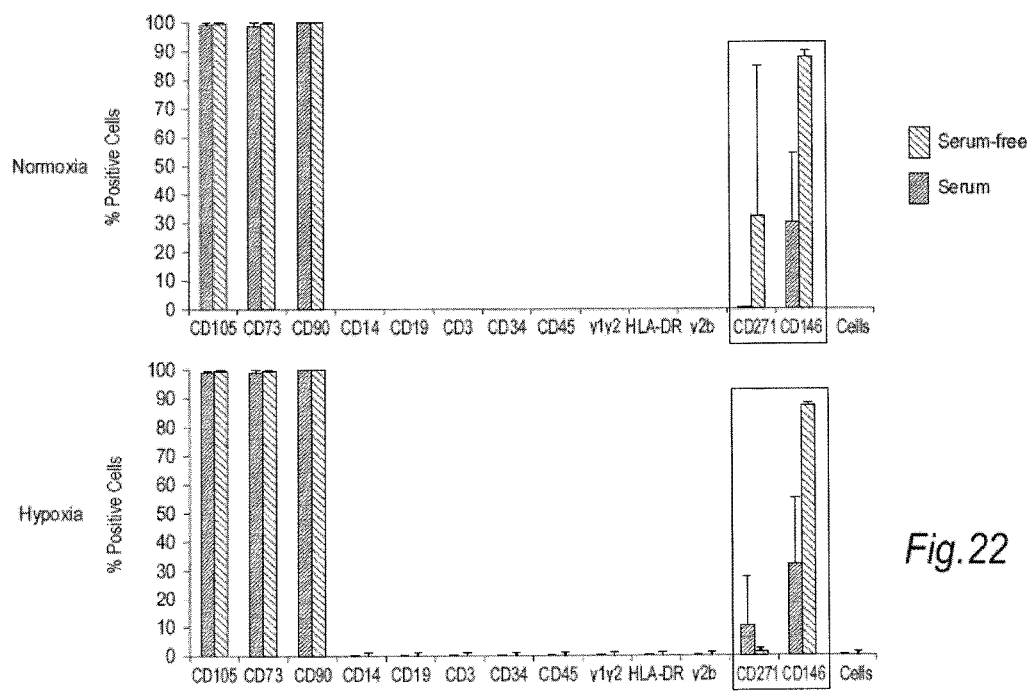

FIG. 10 shows the results of examples in which surface characterisation of MSC isolated in serum-free medium using conditions 7 and 8 as set out in Table 3 at the end of passages 3, 6 and 9. MSC cultured in 10% FBS medium was used as a control;

FIG. 11 shows the results of examples in which differentiation characterisation of MSCs isolated in serum free medium at the beginning of passage 3. MSC cultured in 10% FBS medium was used as a control. The ability of MSC to undergo adipogenesis was shown by the presence of oil red o positive vacuoles (a), alazirin red staining and positive calcium assay confirmed the ability of MSC to undergo osteogenesis (b), chondrogenesis was confirmed by toludine blue staining and quantification of GAG protein (c); results are representative of 4 biological replicates;

FIG. 12 shows differentiation characterisation of MSCs isolated in serum-free medium at the beginning of passage 7. MSC cultured in 10% FBS medium was used as a control. The ability of MSC to undergo adipogenesis was shown by the presence of oil red o positive vacuoles (a), alazirin red staining and positive calcium assay confirmed the ability of MSC to undergo osteogenesis (b), chondrogenesis was confirmed by quantification of GAG protein (c); results are representative of 3 biological replicates;

FIG. 13 shows angiogenic differentiation characterisation of MSC isolated in serum free medium at the beginning of passage 3. MSC cultured in 10% FBS medium was used as a control. MSC were co-cultured with human umbilical vascular endothelial cells (HUVECs) and the number of tubules formed was quantified; results are represented as a percentage where the number of tubules formed by HUVECs alone was set as 100%. Results are representative of 4 biological replicates with n=4;

FIG. 14 shows in vivo differentiation of MSC cultured in serum-free medium to bone tissue;

FIG. 15 shows in vivo differentiation of MSC cultured in serum-free medium to bone tissue;

FIG. 16 shows the growth kinetics and cell morphology of MSCs grown under hypoxic and normoxic conditions using serum-free medium and medium containing serum. FIG. 16A shows the growth kinetics of the MSCs. FIG. 16B shows the cell morphology of the cultured MSCs. FIG. 16C shows the predicted yield of cells from 4 different samples of bone marrow;

FIG. 17 shows osteogenic differentiation of MSCs cultured in serum-free medium vs serum-containing medium under hypoxic and normoxic conditions. 11 Day culture. Mean±SD, n=4 donors. Scale Bar: 500 µm. **: P≤0.05;

FIG. 18 shows adipogenic differentiation of MSCs cultured in serum-free medium vs serum-containing medium under hypoxic and normoxic conditions. Mean±SD, n=4 donors, Scale bar: 500 µm, *: P≤0.5;

FIG. 19 shows chondrogenic differentiation of MSCs cultured in serum-free medium vs serum-containing medium under hypoxic and normoxic conditions. 18 day culture. Mean±SD, Scale bar: 500 µm, n=3 donors;

FIG. 20 shows the pro-angiogenic ability of MSCs cultured in serum-free medium vs serum-containing medium under hypoxic and normoxic conditions. Mean±SD, Scale Bar: 200 µm, n=4 donors;

FIG. 21 shows the degree of immunogenicity of MSCs cultured in serum-free medium vs serum-containing medium under hypoxic and normoxic conditions. Mean±SD. n=3 MSC donors Vs 1 MLR donor. Stats: t tests; ** P<0.05; and FIG. 22 shows the surface cell-marker phenotypes of MSCs cultured in serum-free medium vs serum-containing medium under hypoxic and normoxic conditions. Mean±SD, n=3 donors (P3).

EXAMPLE 1

Figure 1:
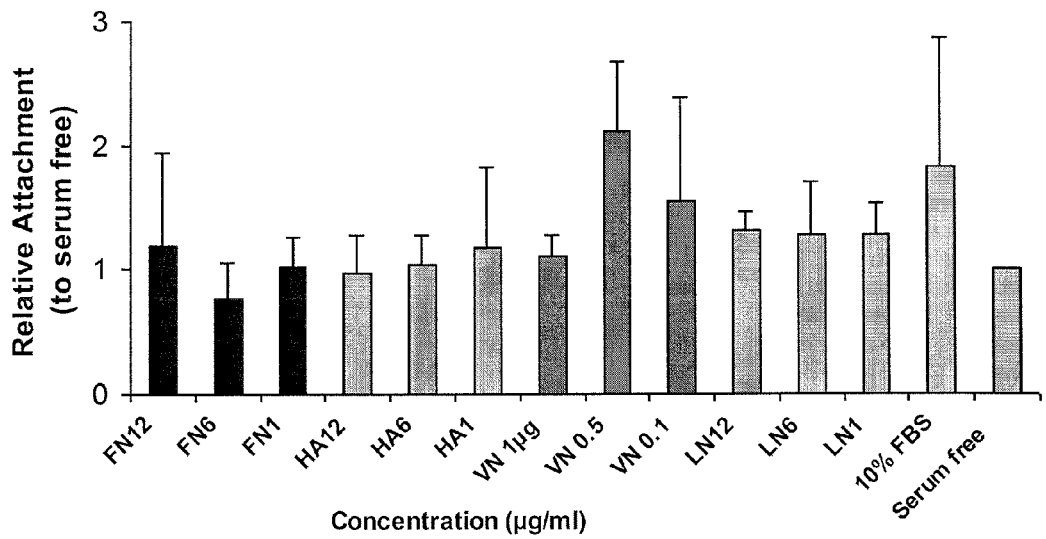
Figure 2:
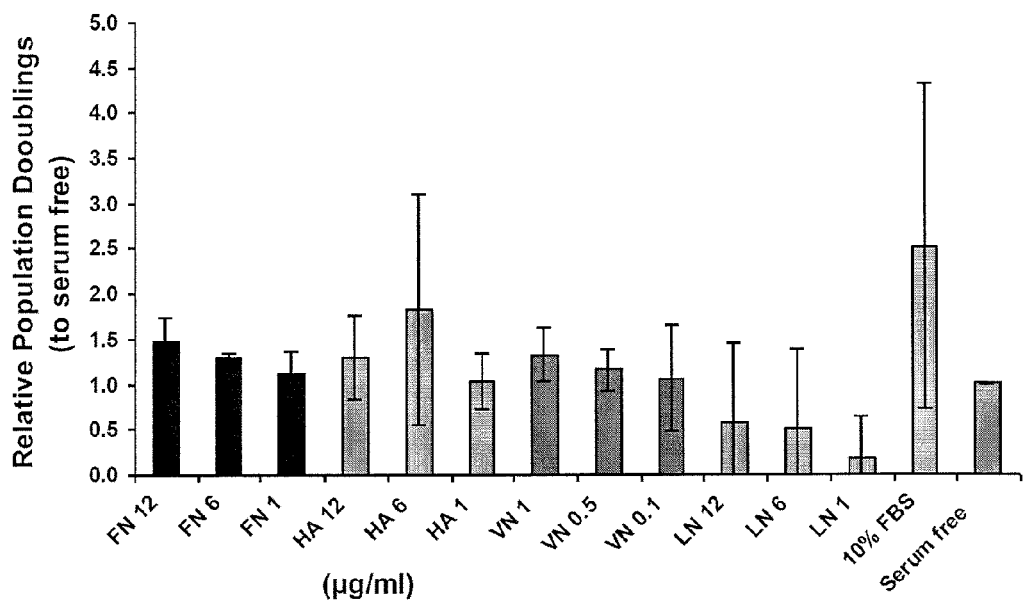

FIG. 1 shows the results of an initial experiment in which the ability of 4 attachment factors to support MSC isolated in the presence of 10% serum to attach in a serum free environment was examined after 18 hours; the factors were: hylauronic acid (HA), fibronectin (FN), vitronectin (VN), laminin (LN) and epidermal growth factor (EGF). Proliferation of the MSC attached in the presence of basic fibroblast growth factor (bFGF2, FGF2) was also assessed after 6 days. Results showed that after 18 hours in a serum-free environment, vitronectin (0.5 µg/ml) supported MSC attachment optimally (FIG. 1); however, fibronectin (6 µg/ml) showed similar MSC yields to vitronectin (0.5 µg/ml) after 6 days (FIG. 2). EGF (10 ng/ml) also increased MSC attachment after over passaging (FIG. 3).

Serum-free basal medium formulation was selected based on the literature describing low-serum cell culture of dental pulp stem cells (Tarle et al., 2010). The basal medium was composed of ITS (1%, BD), ascorbic acid (10 mM, Sigma Aldrich), dexamethasone (10 nM, Sigma Aldrich), human serum albumin (50 mg/ml, Sigma Aldrich), penicillin/streptomycin solution (1%, Gibco) and MEM-α (Gibco). The effect of a range of growth factors on MSC proliferation was then examined. MSC were attached on fibronectin-coated tissue culture plastic for 48 hours in serum-free basal medium.

Ascorbic acid is a vitamin C source. MEM-α is a minimum essential media formulation and a buffer; it also provides, inter alia, amino acids, and is a nutrient. Dexamethasone is a steroid and an oestrogen-like factor, HSA is a protein source, and ITS provides insulin, transferrin (an iron source) and selenic acid.

The basal medium was made up as follows:

| Reagent | Volume (ml) | Final concentration |
| --- | --- | --- |
| MEM-α | 489 | |
| Ascorbic acid 2-phosphate (10 mM) | 5 | 100 µM |
| Dexamethasone | 25 µl | 50 nM |
| Lipoprotein | 20 µl | 40 µg |
| Human Serum Albumin (HSA) | 0.5 | 1% |
| ITS | 0.5 | |
| Penicillin/streptomycin | 5 | 100 U/ml penicillin 100 µg/ml streptomycin |

The effect of FGF2/FGF4 and FGF7 (1, 5 and 10 ng/ml), PDGFaa/PDGFab and PDGFbb (1, 5 and 10 ng/ml) on MSC proliferation over 3 passages on days 5, 10 and 15 was examined. FIG. 4 demonstrates how FGF2 (5 ng/ml), FGF4 (5 ng/ml) and PDGFab (10 ng/ml) increased MSC proliferation in serum free medium.

Figure 5:
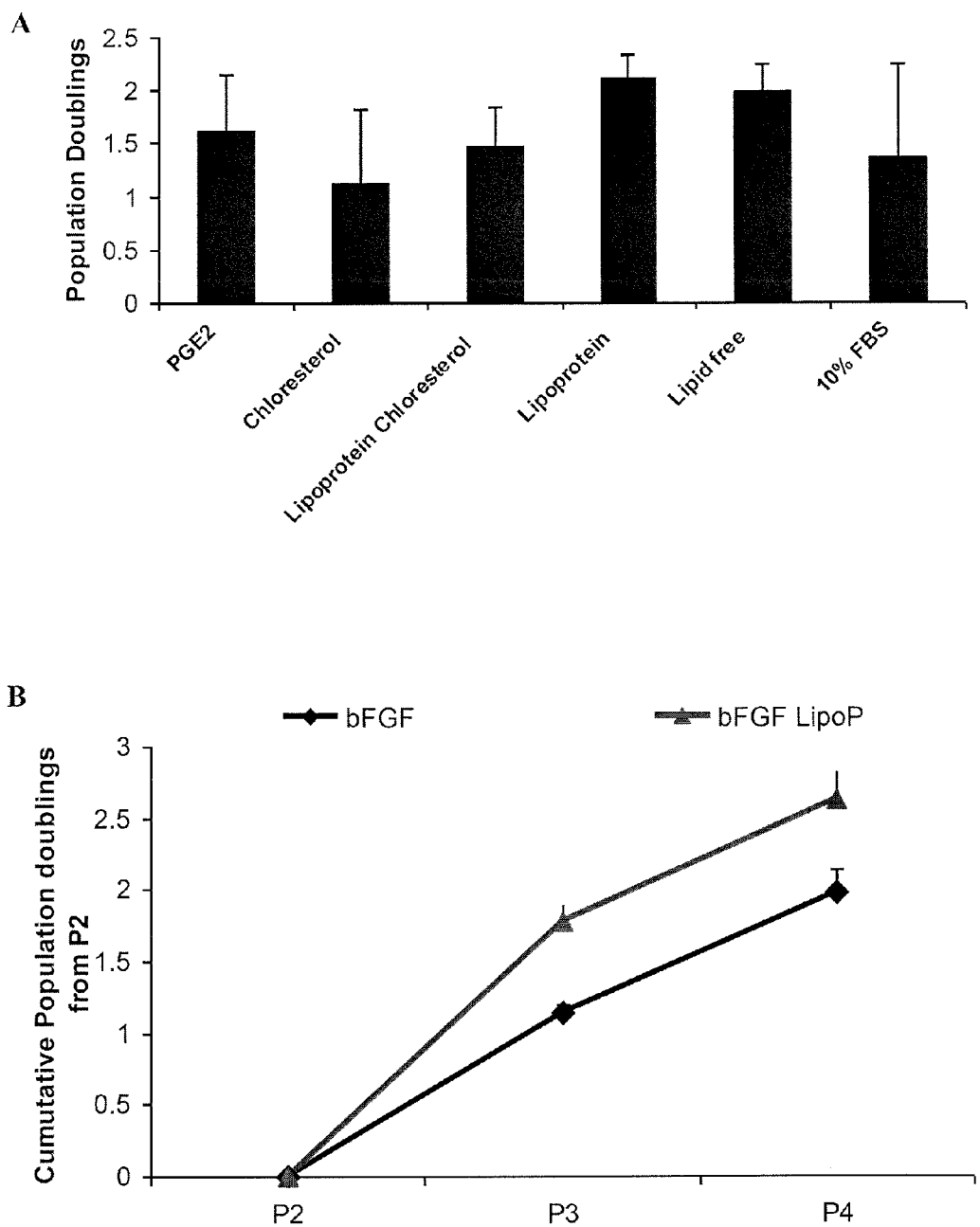

To further enhance MSC viability and proliferation lipoprotein was added to the serum-free basal medium. MSC isolated in the presence of serum were seeded on fibronectin-coated tissue culture plastic in serum free medium containing FGF2. Initially a range of factors were screened to support MSC viability after trypsinisation; the effect of prostoglandin E2 (PGE2; 50 μg/ml), cholesterol (30 μg/ml) and lipoprotein (4 μg/ml) on MSC proliferation in serum free medium containing FGF2 (5 ng/ml) was examined. Lipoprotein low density (40 μg/ml; Sigma-Aldrich) was shown to increase MSC proliferation while PGE2 and cholesterol had an inhibitory effect (FIG. 5a). Lipoprotein increased MSC proliferation over 3 passages in serum-free medium containing FGF2 (FIG. 5b) and was therefore added to the serum-free medium formulation.

Figure 6:
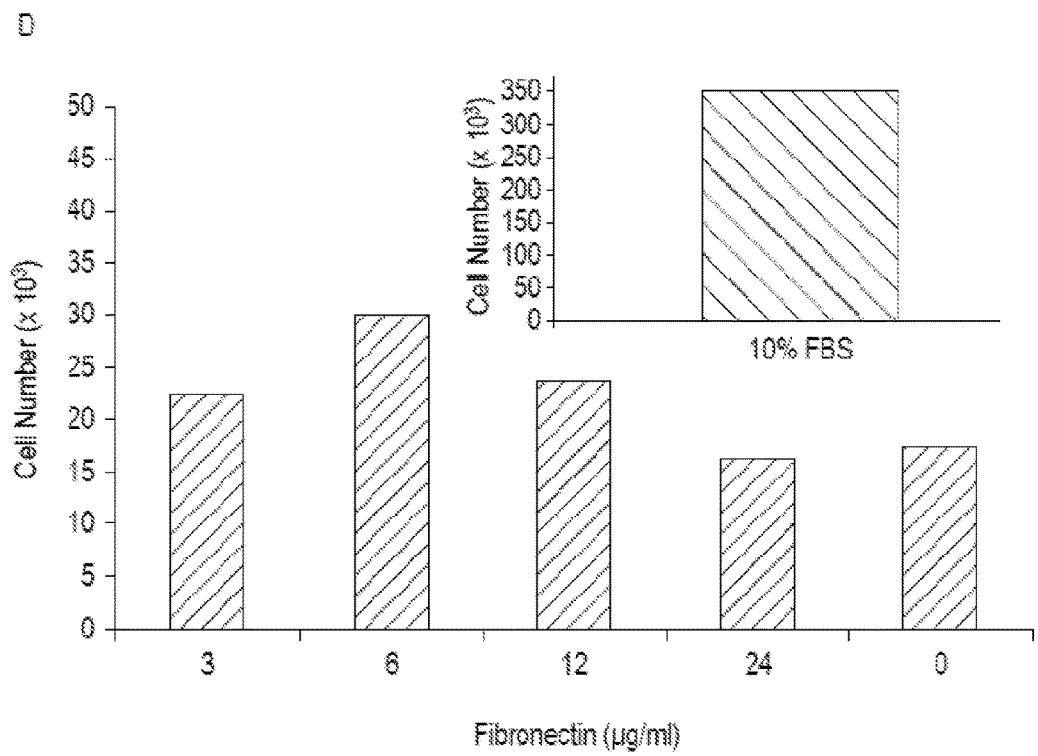

Initially MSC were isolated from three bone marrows to determine a suitable attachment substrate. Vitronectin, hyaluronic acid and fibronectin were screened; fibronectin yielded more colony forming units (FIG. 6A) and the greatest cell number at the end of the first passage (FIG. 6B). A further bone marrow donor was then screened to determine the optimal fibronectin concentration; 6 μg/ml was selected as the favourable concentration (FIGS. 6C and 6D).

To examine the role of EGF in MSC isolation and attachment, 5 bone marrows were tested. MSC were isolated in the presence of FGF2 (5 ng/ml) on fibronectin coated plastic in the presence of EGF, or on tissue culture plastic in the presence of EGF. The results showed variability between bone marrow donors however it was concluded that fibronectin was required in this particular case for MSC attachment (FIGS. 7A and 7B).

To evaluate the effect of growth factors on MSC proliferation, 4 bone marrows were seeded on fibronectin-coated tissue-culture plastic in serum free basal medium as is shown in table 1.

TABLE 1

Growth factors added to serum free basal medium.

| Condition | Additional growth factors |
|---|---|
| 1 | FGF2 (5 ng/ml) |
| 2 | FGF2 (5 ng/ml), EGF (10 ng/ml) |
| 3 | FGF2 (5 ng/ml), FGF4 (5 ng/ml) |
| 4 | FGF2 (5 ng/ml), FGF4 (5 ng/ml), EGF (10 ng/ml) |
| 5 | FGF2 (5 ng/ml), PDGFab (10 ng/ml) |
| 6 | FGF2 (5 ng/ml), PDGFab (10 ng/ml), EGF (10 ng/ml) |
| 7 | FGF2 (5 ng/ml), TGFβ1 (5 ng/ml) |
| 8 | FGF2 (5 ng/ml), TGFβ1 (5 ng/ml) EGF (10 ng/ml) |
| 9 | 10% FBS |

Figure 8:
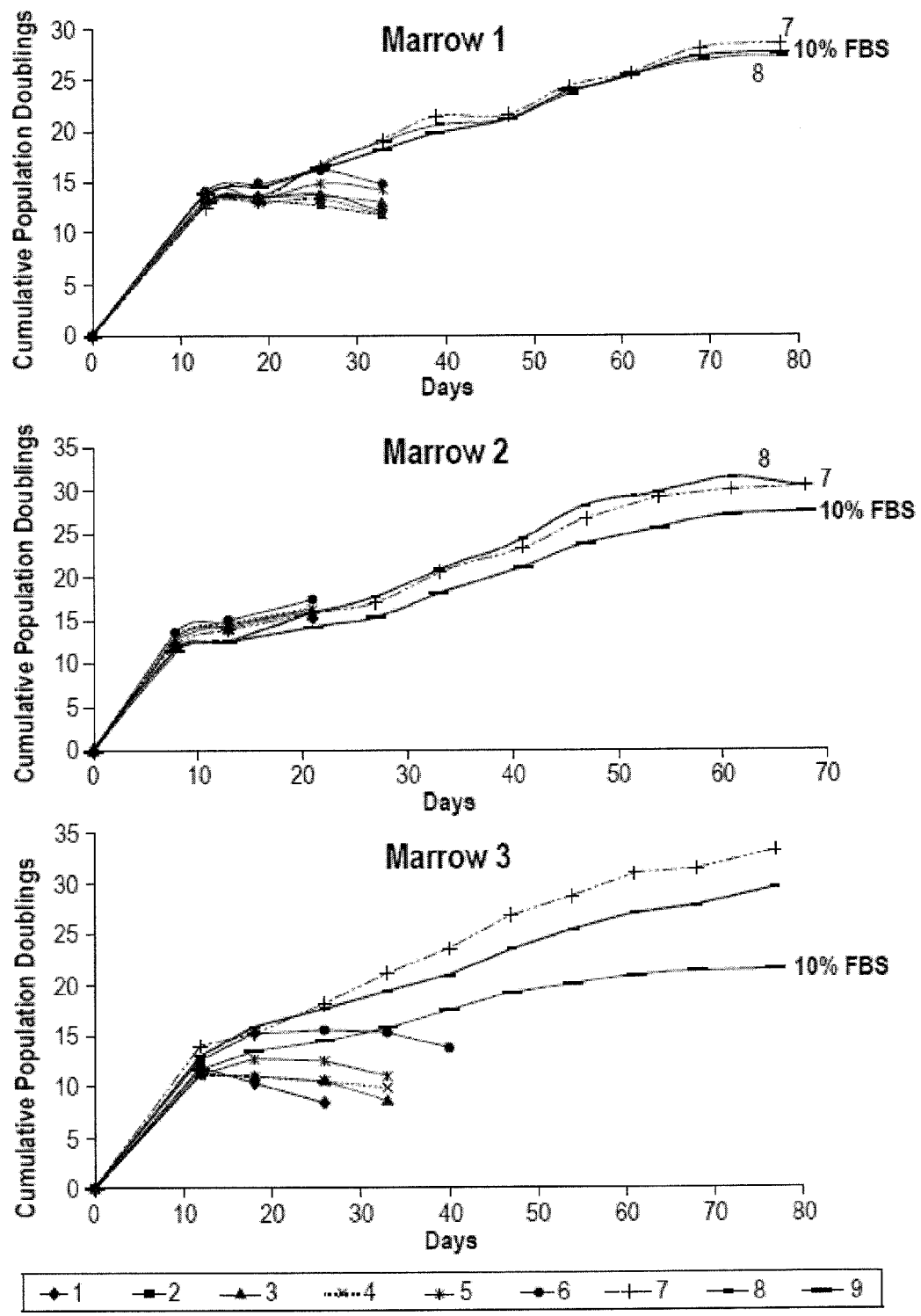
FIG. 8 shows the results of examples in which MSC were isolated on tissue culture plastic pre-coated with fibronectin (6 µg/ml) in serum-free media containing growth factors as set out in Table 1. Cells were trypsinised at the end of each passage and seeded on fibronectin-coated plastic; control cells were seeded on tissue culture plastic in 10% FBS.

MSC yield after the first passage indicated no difference in the conditions, however, after passage 3 conditions 1-6 inclusive decreased in cumulative population doublings. Conditions 7, 8 and 9 showed a steady increase over the all the conditions (FIG. 8, marrows 1, 2 and 3). The yield of cells from these cultures is shown in Table 2 (NB Thus, medium 1 and 2 in Table 2 correspond to Medium 7 and 8 in Table 1 respectively).

In addition, the serum free medium was shown to be superior to FBS in promoting isolation and proliferation of MSCs from five donors with growth maintained to passage 10. Furthermore, MSC yield was ten times greater in serum free medium at the end of passage 3 and up to 100 times greater at the end of passage 6 in comparison to cultures grown in FBS.

To further evaluate MSC proliferation an additional bone marrow was seeded on fibronectin-coated tissue-culture plastic in serum free basal medium as is shown in Table 3.

TABLE 3

Growth factors added to serum free basal medium.

| Condition | Additional growth factors |
|---|---|
| 5 | FGF2 (5 ng/ml), PDGFab (10 ng/ml) |
| 6 | FGF2 (5 ng/ml), PDGFab (10 ng/ml), EGF (10 ng/ml) |
| 7 | FGF2 (5 ng/ml), TGFβ1 (5 ng/ml) |
| 8 | FGF2 (5 ng/ml), TGFβ1 (5 ng/ml), EGF (10 ng/ml) |
| 10 | FGF2 (5 ng/ml), TGFβ1 (5 ng/ml), PDGFab (10 ng/ml) |
| 11 | FGF2 (5 ng/ml), TGFβ1 (5 ng/ml), PDGFab (10 ng/ml), EGF (10 ng/ml) |
| 9 | 10% FBS |

Figure 9:
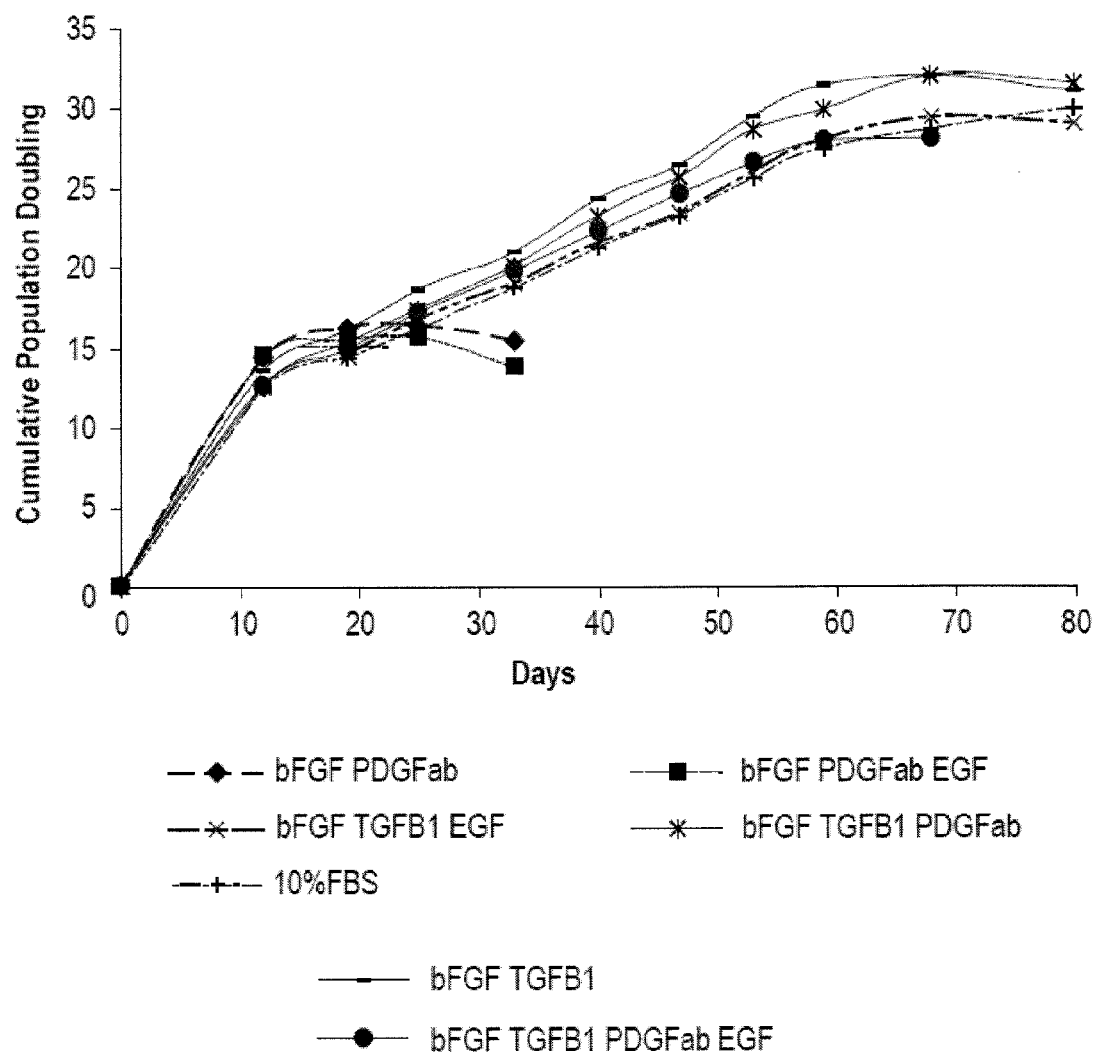
FIG. 9 shows the results of examples in which MSC were isolated on tissue culture plastic pre-coated with fibronectin (6 µg/ml) in serum-free media containing growth factors as set out in Table 3. Cells were trypsinised at the end of each passage and seeded on fibronectin-coated plastic; control cells were seeded on tissue culture plastic in 10% FBS.

MSC yield after the first passage indicated no apparent difference in the conditions, however, after passage 2 conditions 5 and 6 decreased in cumulative population doublings. Conditions 7, 8, 9, 10 and 11 showed a steady increase in population doublings, however, the addition PDGFab (conditions 10 and 11) did not increase MSC yield in comparison to conditions 7 and 8 (FIG. 9).

MSC surface phenotype characterisation was carried out using a panel of antibodies for the detection of positive and negative markers; this analysis was carried out at the end of passages 3, 6 and 9. FIG. 10 illustrates no difference in the standard panel of surface marker expression in MSCs cultured in serum free media (conditions 7 and 8) in comparison to MSCs cultured in 10% FBS. In addition MSC markers CD90, CD73 or CD105 remained positive at passage 3, passage 6 and passage 9. However, MSC cultured in the serum free conditions 7 and 8 showed higher CD146 expression in comparison to serum cultured cells and this is preserved over passaging.

To further investigate MSC phenotype, MSC were seeded into adipogenesis, osteogenesis and chondrogenesis assays at the beginning of passage 3. FIG. 11 shows no difference in the ability of the different MSC cultures to form adipocytes (FIG. 11a), osteocytes (FIG. 11b) or chondrocytes (FIG. 11c).

To investigate MSC phenotype stability, MSC were seeded into the adiopgenesis, osteogenesis and chondrogen-

TABLE 2

Predicted yield of cells per ml for the experiments of FIG. 8

| | +Serum (10% FBS) | | | Serum-Free (Medium 1) | | | Serum-Free (Medium 2) | | |
|---|---|---|---|---|---|---|---|---|---|
| | Marrow 1 | Marrow 2 | Marrow 3 | Marrow 1 | Marrow 2 | Marrow 3 | Marrow 1 | Marrow 2 | Marrow 3 |
| P0 | 2.40E+05 | 1.96E+06 | 4.69E+05 | 3.18E+06 | 1.20E+06 | 2.66E+06 | 1.72E+06 | 2.54E+06 | 1.49E+06 |
| P1 | 4.74E+05 | 3.17E+06 | 1.04E+06 | 2.38E+07 | 1.89E+06 | 6.02E+06 | 1.22E+07 | 3.87E+06 | 3.14E+06 |
| P2 | 1.22E+06 | 1.23E+07 | 1.81E+06 | 1.83E+08 | 2.27E+07 | 5.62E+07 | 4.07E+07 | 3.27E+07 | 1.94E+07 |
| P3 | 3.12E+06 | 3.84E+07 | 4.50E+06 | 1.56E+09 | 1.15E+08 | 3.15E+08 | 2.23E+08 | 1.70E+08 | 1.09E+08 |
| P4 | 9.99E+06 | 1.34E+08 | 1.64E+07 | 8.86E+09 | 5.50E+08 | 1.10E+09 | 6.99E+08 | 5.20E+08 | 4.72E+08 |
| P5 | 3.20E+07 | 3.28E+08 | 4.01E+07 | 7.56E+10 | 6.36E+09 | 9.10E+09 | 3.84E+09 | 7.40E+08 | 2.41E+09 |
| P6 | 5.54E+07 | 2.15E+09 | 1.55E+08 | 2.69E+11 | 4.07E+09 | 6.19E+10 | 1.45E+10 | 4.34E+09 | 1.61E+10 |
| | | 7.9E+08 | | | 1.1E+11 | | | 1.2E+10 | | esis assays again at the beginning of passage 7. FIG. 12 shows MSC retain their ability to differentiate after subsequent passaging and there is no difference between the different cultures to form adipocytes (FIG. 12a), osteocytes (FIG. 12b) or chondrocytes (FIG. 12c).

To investigate the angiogenic potential of the different MSC cultures, MSCs at the beginning of passage 3 were co-cultured with human umbilical vascular endothelial cells (HUVECs) on a matrigel. After 4 hours the number of tubules formed was quantified. To further assess the secretion of angiogenic factors by the MSC cultures, MSC media from 2 day old MSC cultures was added to HUVECs on a similar matrigel.

FIG. 13 shows that MSC cultured in serum free media containing bFGF and TGFβ-1 with or without EGF form more tubules then MSC cultured in 10% FBS. Furthermore media from these cultures also supported tubule formation, thus suggesting the release of angiogenic factors by these serum-free cultures.

FIGS. 14 and 15 show in vivo differentiation of MSC cultured in serum-free medium to bone tissue. The bone tissue produced was superior to that of the control experiment in which MSC were cultured in serum-containing medium.

In order to investigate whether culture of MSC under hypoxic conditions increases cell yield and/or maintains the characteristics of bone marrow-derived serum-free MSCs, a complete characterisation of serum-free medium was performed including the following investigations: growth kinetics, cell morphology, tri-lineage differentiation potential, surface phenotype, pro-angiogenic potential and immunological properties. The results of these experiments are shown in FIG. 16 and demonstrate that hypoxia-cultured, serum-free-medium cells have superior growth kinetics and also produce a greater yield of cells than cells cultured using control, serum-containing medium.

EXAMPLE 2

Aims and Methods

The following was performed to assess the effect of media of the invention containing various lipoproteins on proliferation, differentiation, cell morphology and surface maker phenotype of bone marrow-derived MSCs and to assess the requirement for an attachment factor, namely fibronectin, for use with the serum-free medium.

Medium Preparation

For the lipoprotein study, Serum Free (SF) media was prepared containing: no lipoprotein (No lipo), very low density lipoprotein (VLDL), low density lipoprotein (LDL) and high density lipoprotein (HDL). Other lipoproteins that exist are chylomicrons and intermediate density lipoprotein which were not assessed in this study as they were not commercially available at the time.

MSC Culture

MSCs were isolated from bone marrow based on plastic adherence in SF medium by plating $40 \times 10^6$ human bone marrow mononuclear cells/T-175 and culturing at 37° C., 5% $CO_2$, 21% $O_2$. Cells were subcultured once they had reached 80-90% confluence. MSCs were evaluated by assessing growth kinetics, tri-lineage differentiation and surface marker phenotype at the end of passage 3 (P3). For the lipoprotein study, SF medium was modified to contain one of the various lipoproteins at 80 ng/mL and these cells are seeded onto T175 flasks, which had been pre-coated with fibronectin. For the fibronectin study described, standard SF medium containing LDL (Standard Formulation) was used and cells were seeded onto T175 flasks without fibronectin, with fibronectin pre-coating or with fibronectin added to the medium itself.

For passaging of SF cells, media was aspirated and 5 ml of TrypLE was added per one T175 flask. Flasks were incubated 10 min at room temperature and viewed under the microscope for detachment. Once cells detached, 5 ml of media was added and cell suspension was transferred to a 50 ml centrifuge tube and centrifuged at 400×g for 5 min. Cells were grown to passage 3 (P3) at which point they were used for tri-lineage differentiation studies or used to assess and flow cytometry analysis.

Flow cytometry analysis of cell samples was performed as outlined below. Blocking solution was prepared by adding 1 mL of mouse serum to 49 mL of D-PBS in a 50 mL tube. FACS buffer was 2% HSA solution prepared in D-PBS.

MSC Staining $1 \times 10^5$ cells (100 μL) was pipetted into each of 8 wells of the 96-well plate on ice, one for each antibody and one for unstained cells. The plate was then centrifuged for 4 mins at 400 g, 4° C. The supernatant was aspirated carefully to not disturb cell pellet and 50 μL of blocking solution was added to each well, and the pellet resuspended by pipetting the solution. Samples were incubated for 1 hr in blocking solution. After blocking, plates were centrifuged as before and resuspended in 50 uL of FACS buffer containing the appropriate antibody. Samples were incubated with antibodies for 45 mins at 4° C. in the dark. After incubation with antibodies, samples were washed three times with FACS buffer before finally being resuspended in 200 μL FACS buffer and transferred to a FACS tube. Sytox Red viability dye was also added to the samples at a final dilution of 1:10,000, 10 mins prior to assessing marker expression using a BD FACS Canto II.

Results

CFU-f assays were carried out by seeding bone marrow mononuclear cells (MNCs) at a density of $1 \times 10^6$ MNC/10 $cm^2$ in triplicate in 6-well plates. On day 10, cells were fixed using pre-cooled 95% methanol and stained with 2% crystal violet for 10 mins. Samples were then washed with PBS and imaged. HDL groups contained densely packed CFU-fs whereas VLDL and LDL groups contained dispersed colonies.

MSCs were isolated from bone marrow and plated directly onto fibronectin pre-coated tissue culture plastic in SF medium with or without the various lipoproteins listed above. An increase in CFU-f numbers was observed in the groups containing VLDL and LDL (approximately 3-5 fold compared with HDL).

MSC markers CD105, CD73 and CD90 were assessed and normalised to their isotype control used at the same concentration. Equivalent expression of these markers was observed. In addition, CD146, CD271 and W8B2 were assessed. These are markers which previously have been shown to be maintained in SF-cultured MSCs and are lost or greatly reduced in the presence of serum. Expression of these markers varied greatly between donors but no changes were observed in MSCs exposed to the different lipoproteins or in their absence.

MSCs were isolated from bone marrow and plated directly onto tissue culture plastic without precoating with fibronectin, with precoating of the flask with fibronectin or with fibronectin added to the media formulation itself. No difference was observed in the ability of CFU-fs to form with or without the presence of fibronectin in the system, whether it is included in the medium or used as a separate pre-coating step.

CONCLUSIONS

The work described above set out to compare different specific lipoprotein in the serum-free and assess the requirement of fibronectin as an attachment factor.

CFU-fs in the presence of HDL-containing SF medium formed CFU-fs with dense clusters of cells with sparse outgrowth of cells. Conversely MSCs isolated with VLDL-containing SF medium or LDL-containing SF medium formed CFU-fs with dispersed colonies where cells were predominantly seen as single cells. VLDL and LDL are involved in trafficking fats to cells in arteries which may indicate why these groups had cells which formed more disperse healthier looking CFU-fs. However, the cells at P3 all have a similar cell morphology to each other which may indicate that one requirement for lipoprotein may only be in the initial isolation of MSCs (in this case from bone marrow). There was an increase in CFU-f numbers in groups containing either VLDL or LDL. Applying these CFU-f numbers with cell yields at the end of each passage, growth curves were calculated. No intra donor difference was observed between lipoprotein groups and inter donor differences in growth kinetics was consistent with multiple MSC donors.

To further investigate the effect of lipoprotein on MSCs, tri-lineage differentiation assays were carried out. Chondrogenesis was assessed by measuring levels of sulphated glycosaminoglycan levels normalised to DNA content. Based on these results, no statistical difference was observed between all groups. Similarly, osteogenic potential of the cells was assessed. Cells were cultured in standard osteogenic medium for 10 days and osteogenesis was assessed by measuring calcium levels as an indicator of mineralised matrix formed. No statistical difference was observed within these groups. Adipogenesis was assessed by measuring fat formation which stains red when stained with Oil Red O. As with osteogenesis and chondrogenesis, there was no statistical difference in the adipogenic potential of MSCs cultured with various lipoproteins.

In addition to their tri-lineage potential, MSCs are characterised by their co-expression of CD90, CD105 and CD73. In addition to this, we have observed that SF-cultured MSCs maintain expression of CD271, CD146 and W8B2, markers indicative of the in vivo MSC which are typically lost or reduced significantly early on during in vitro culturing. All lipoprotein treated cells maintained expression of the MSC markers CD105, CD73 and CD90 above 95%. Expression of CD271, CD146 and W8B2 was also maintained in all groups but at highly variable levels. However it is worth noting that there was no intra donor difference of these markers due to presence of various lipoproteins.

Based on the results outlined above, lipoprotein appears to have no effect on surface marker expression of MSCs, growth kinetics or tri-lineage differentiation potential. However, the presence of lipoprotein seems to be important for initial isolation of MSCs from bone marrow. Colonies established in HDL-containing SF medium have tightly packed colonies which appear stressed and do not maintain the normal CFU-f morphology. Moreover, yields of CFU-fs obtained increased when isolated in VLDL or LDL. Based on the data mentioned above, VLDL or LDL appears to be more suitable for use in the serum-free medium compared to HDL.

The final aim of this work was to determine if fibronectin is required for isolation and establishment of MSC cultures in the proprietary serum-free medium. The incorporation of fibronectin in the SF medium was also included in the comparison to the standard practice of pre-coating culture surfaces with the attachment factor. This was assessed by looking at CFU-f numbers and growth kinetics of cells isolated from bone marrow directly onto tissue culture plastic without fibronectin, onto tissue culture plastic pre-coated with fibronectin and finally with fibronectin incorporated into the medium itself. No difference was observed in CFU-f numbers isolated from bone marrow normalised to MNC count. Similarly, growth kinetics of the MSC cultures were unaffected by the presence or absence of fibronectin indicating that an attachment factor is not required for isolation or proliferation of MSCs in the serum-free medium of the invention.

Accordingly, the invention provides a medium for the growth of stem cells without the use of serum as a component of the medium, methods for utilising this medium and cells produced using this medium.

The invention claimed is:

1. A serum-free medium for culturing mesenchymal stem cells, comprising:
   (i) as growth factors,
   (a) fibroblast growth factor (FGF) and (b) transforming growth factor beta (TGFβ), and no other growth factors; and
   (ii) a basal medium supplemented with lipoprotein, insulin-transferrin-selenium (ITS), ascorbic acid, dexamethasone, human serum albumin, penicillin and streptomycin.

2. The medium according to claim 1, wherein the medium comprises the lipoprotein at a concentration of from 1 μg/ml to 100 μg/ml.

3. The medium according to claim 1, wherein the lipoprotein component of the medium comprises one or more selected from the group consisting of:
   high-density lipoprotein (HDL);
   low-density lipoprotein (LDL);
   intermediate-density lipoprotein (IDL); and
   very-low-density lipoprotein (VLDL).

4. The medium according to claim 3, wherein said medium comprises LDL.

5. The medium according to claim 4, wherein the LDL comprises one or more or all of the following:
   large buoyant LDL (lb LDL) particles;
   small dense LDL (sd LDL) particles; and
   lipoprotein(a) (Lp(a)).

6. The medium according to claim 4, wherein said medium comprises LDL particles of diameter from 15 nm to 30 nm.

7. The medium according to claim 3, wherein said medium comprises VLDL.

8. The medium according to claim 7, wherein said medium comprises VLDL particles of diameter from 30 nm to 80 nm.

9. The medium according to claim 4, wherein the FGF component of the medium is FGF2 (bFGF), optionally at a concentration of 1 to 10 ng/ml.

10. The medium according to claim 4, wherein the TGFβ component of the medium is TGFβ-1, optionally at a concentration of 1 to 20 ng/ml.

11. A method of culturing a mesenchymal stem cell comprising incubating the stem cell in the serum-free medium according to claim 4.

12. A composition comprising a mesenchymal stem cell, in the serum-free medium according to claim 1.

13. The medium according to claim 4, further comprising a human mesenchymal stem cell.

14. The composition according to claim 12, wherein the mesenchymal stem cell is a human mesenchymal stem cell.

15. A serum-free medium for culturing mesenchymal stem cells consisting of:
fibroblast growth factor (FGF);
transforming growth factor beta (TGF-β); and
a basal medium supplemented with lipoprotein, insulin-transferrin-selenium (ITS), ascorbic acid, dexamethasone, human serum albumin, penicillin and streptomycin.

\* \* \* \* \*